United States Patent
Carter et al.

(10) Patent No.: US 6,584,358 B2
(45) Date of Patent: Jun. 24, 2003

(54) ELECTRO THERAPY METHOD AND APPARATUS

(75) Inventors: John Carter, Belle Harbor, NY (US); Bradford Siff, Weston, CT (US)

(73) Assignee: Biowave Corporation, Norwalk, CT (US)

(*) Notice: Subject to any disclaimer, the term of this patent is extended or adjusted under 35 U.S.C. 154(b) by 174 days.

(21) Appl. No.: 09/756,999

(22) Filed: Jan. 8, 2001

(65) Prior Publication Data

US 2001/0031999 A1 Oct. 18, 2001

Related U.S. Application Data

(60) Provisional application No. 60/183,258, filed on Feb. 17, 2000, and provisional application No. 60/175,003, filed on Jan. 7, 2000.

(51) Int. Cl.⁷ .................................................. A61N 1/34
(52) U.S. Cl. ...................... 607/69; 607/46; 607/72; 607/74; 607/76
(58) Field of Search ........................... 607/46, 67, 69–70, 607/72, 74, 76

(56) References Cited

U.S. PATENT DOCUMENTS

| | | | |
|---|---|---|---|
| 2,622,601 A | 12/1952 | Nemec | 128/422 |
| 3,096,768 A | 7/1963 | Griffith, Jr. | 128/422 |
| 3,170,993 A | 2/1965 | Puharich et al. | 179/107 |
| 3,393,279 A | 7/1968 | Flanagan | 179/107 |
| 3,563,246 A | 2/1971 | Puharich | 128/422 |
| 3,586,791 A | 6/1971 | Puharich | 179/107 |
| 3,727,616 A | 4/1973 | Lenzkes | 128/422 |
| 3,774,620 A | 11/1973 | Hansjurgens | 128/419 |
| 3,794,022 A | 2/1974 | Nawracaj et al. | 128/422 |
| 3,958,577 A | 5/1976 | Rodler | 128/422 |
| 4,023,574 A | 5/1977 | Nemec | 128/420 |
| 4,071,033 A | 1/1978 | Nawracaj et al. | 128/420 |
| 4,153,061 A | 5/1979 | Nemec | 128/420 |
| 4,177,819 A | 12/1979 | Kofsky et al. | 128/422 |
| 4,220,830 A | 9/1980 | Schafer | 179/107 |
| 4,280,504 A | 7/1981 | Rodler | 128/420 |
| 4,401,121 A | 8/1983 | Rodler | 128/420 |
| 4,580,570 A | 4/1986 | Sarrell | 128/421 |
| 4,595,010 A | 6/1986 | Radke | 128/421 |
| 4,711,243 A | 12/1987 | Schafer | 128/420 |
| 4,848,347 A | * 7/1989 | Hall | 128/420 |
| 4,909,255 A | 3/1990 | Farin | 128/420 |
| 4,960,124 A | 10/1990 | Masaki | 128/421 |
| 4,977,895 A | 12/1990 | Tannenbaum | 128/421 |
| 4,989,605 A | 2/1991 | Rossen | 128/422 |
| 5,107,835 A | 4/1992 | Thomas | 128/419 |

(List continued on next page.)

OTHER PUBLICATIONS

Electro–Acuscope 70C Specifications—Biomedical Design Instruments "Electro–Acuscope 70" http://www.designmed.com/70c.htm, (4 pages).

Electro–Acuscope 80L Electro–Myopulse 75L; http://www.acuscope.com/italy/it1.htm, (8 pages).

*Primary Examiner*—Teresa Walberg
*Assistant Examiner*—Shawntina Fuqua
(74) *Attorney, Agent, or Firm*—Pennie & Edmonds LLP

(57) ABSTRACT

An electro-therapy apparatus and method for providing therapeutic electric current to a treatment site of a patient, having means for providing two oscillating or pulsing electric alternating currents, of frequencies which differ from each other by as little as 1 Hz and up to about 250 Hz, but each being of frequency at least about 1 KHz. The apparatus and method requires only one feed electrode adapted to feed the electric currents to selected feed sites on or beneath the epidermal or mucous surface of the patient, and only one return electrode adapted to be positioned on or beneath the epidermal or mucous surface of the patient, locally to the treatment site. The apparatus includes a feedback subsystem to detect impedance changes in the patient and accordingly adjust the output of the apparatus.

36 Claims, 13 Drawing Sheets

U.S. PATENT DOCUMENTS

| | | |
|---|---|---|
| 5,161,530 A | 11/1992 | Gamble ..................... 128/420 |
| 5,269,304 A * | 12/1993 | Matthews ................... 607/46 |
| 5,324,317 A | 6/1994 | Reiss ........................ 607/67 |
| 5,458,625 A | 10/1995 | Kendall ..................... 607/746 |
| 5,512,057 A | 4/1996 | Reiss et al. ................ 607/67 |
| 5,573,552 A | 11/1996 | Hansjurgens ............... 607/68 |
| 5,593,432 A | 1/1997 | Crowther et al. ........... 607/46 |
| 5,643,330 A | 7/1997 | Holsheimer et al. ........ 607/46 |
| 5,713,922 A | 2/1998 | King ........................... 607/2 |
| 5,776,173 A * | 7/1998 | Madsen, Jr. et al. ........ 607/67 |
| 5,782,873 A | 7/1998 | Collins ........................ 607/2 |
| 5,948,007 A | 9/1999 | Starkebaum et al. ........ 607/67 |
| 5,950,635 A | 9/1999 | Garcia-Rill et al. ........ 128/898 |
| 5,983,141 A | 11/1999 | Sluijter et al. ............. 607/100 |
| 6,011,994 A | 1/2000 | Kronberg ................... 607/66 |
| 6,058,577 A | 5/2000 | Ida et al. .................... 24/306 |
| 6,064,911 A | 5/2000 | Wingrove ................... 607/46 |
| 6,161,048 A | 12/2000 | Sluijter et al. ............. 607/100 |
| 6,169,813 B1 | 1/2001 | Richardson et al. ........ 381/312 |

* cited by examiner

ELECTRO THERAPY METHOD AND APPARATUS

CROSS REFERENCE TO RELATED APPLICATIONS

This Application claims priority from U.S. provisional applications Ser. No. 60/175,003 filed on Jan. 7, 2000 and Ser. No. 60/183,258 filed on Feb. 17, 2000.

BACKGROUND OF THE INVENTION

This invention relates to an electro-therapy method and apparatus and more particularly to a method and apparatus for relieving pain arising from temporary or chronic conditions or during or after surgery.

Nemec in U.S. Pat. No. 2,622,601 issued on Dec. 23, 1952 disclosed one of the earliest electro therapy apparatuses and method. The Nemec system disclosed an apparatus comprising at least two means for producing alternating currents of frequencies between 1000 and 10,000 cycles with each of means connected with a separate pair of electrodes. The difference frequency between the means was made less than 100 cycles. The electrodes were placed upon the patient such that the two currents would intersect at a proposed therapeutic site. The basic concept was that the higher frequencies would be transmitted, but the low frequency need for therapeutic action would occur only at the common transmission point.

Nemec in U.S. Pat. No. 4,023,574 issued May 17, 1977 disclosed three separate pairs of electrodes are attached to a body part to be treated, spaced apart around said part of the body. A primary alternating electrical current having a primary frequency of between 100 Hz and 100,000 Hz is passed between one of the electrode pairs. A similar second alternating electrical current having a secondary frequency in the same range as the primary frequency but differing by between 50 Hz and 100 Hz from the primary frequency is passed between another of the pairs of electrodes. A tertiary alternating current is passed between the third pair of electrodes and has a tertiary frequency differing by at most 1 Hz from the frequency of either the primary current, the secondary current, or the arithmetic means of the frequency of these two currents.

Hunsjurgens' U.S. Pat. No. 3,774,620 issued on Nov. 27, 1973 disclosed an electro-medicinal apparatus for use in interference current therapy. The apparatus has at least two circuits that act on the patient through electrodes, the currents producing s stimulus active interference on a target area on the patient by superimposing the two or more currents, which by themselves have no stimulating effect, the currents differing from each other by a low frequency value. A particular feature of the apparatus is that the circuits produce an optimum interference at the treatment area and include a current strength-regulating member, which can operate during treatment.

Rodler disclosed in U.S. Pat. No. 3,958,577 issued on May 25, 1976 an apparatus for producing interference and beat-currents in a selectable point of the body, particularly for electrotherapy on the human body, which comprises at least two pairs of electrodes adapted to be applied to the human body. Each of the pairs of electrodes has associated therewith an output amplifier. The latter supplies independently selectively pulse and alternating current for each pair of the electrodes. A voltage proportional in amplitude to the current flowing through the patient is taken. The voltage relates mathematically each individual setting voltage with a common setting and is subtracted. The difference voltage is produced separately for each circuit and used for the amplification control on the corresponding of the amplifiers, and the voltage is so polarized that an increase in patient current resulting in a decrease of the amplification and an increase in the joint voltage resulting in an increase of the amplification.

Nawracaj et al. disclosed in their U.S. Pat. No. 4,071,033 issued on Jan. 31, 1978 that a master oscillator, whose output is split and applied to two frequency dividers that divide the frequency by different numbers, initiates stimuli. The two frequencies thus derived are applied to wave shapers to provide a desired waveform such as a half sine wave, and also each signal is further divided by a common number. The two signals are then amplified, and applied to the body through a probe whose contacts are arranged so that the two stimuli currents are orthogonal to each other. The two high frequency signals heterodyne within the human muscle to produce a single low frequency stimuli, useful for the production of muscle contraction, hyperemia, electro analgesia and muscle relaxation.

Masaki disclosed in U.S. Pat. No. 4,960,124 issued on Oct. 2, 1990 a apparatus for low-frequency electrotherapy wherein the output current of a low-frequency oscillator is applied to the subjects body through a pair of electrodes placed on the subject's body, comprising a first oscillator circuit that generates a low-frequency square wave voltage when the load is in connection with the electrode pair; and a second oscillator circuit that generates a therapeutic voltage when the output voltage of the first oscillator circuit is not zero.

Matthews' U.S. Pat. No. 5,269,304 issued on Dec. 14, 1993 discloses an electrotherapy apparatus that includes at least two electrodes adapted to feed oscillating current to selected sites on or beneath the epidermal or mucous surface remote from a treatment site. A common return electrode is provided at the treatment site that is subjected to the sum of the currents from the two feed electrodes. The feed electrodes may be contact feed electrodes or capacitive feed electrodes. The feed electrodes may operate at different frequencies so that the treatment site is stimulated by the beat frequency. This may be at or about 80 or 130 Hz, if an anaesthetizing effect is required.

Reiss' U.S. Pat. No. 5,324,317 issued on Jun. 28, 1994 discloses an interferential stimulator for applying two medium frequency alternating currents of slightly differing frequencies to the body of a living being so that they cross and interact to produce a low frequency therapeutic current at a selected point. A fixed frequency is generated and applied to the skin through a first electrode pair. A second frequency, differing from the first by from about 1 to 150 Hz is applied through a second electrode pair. The electrodes are arranged to deliver a localized stimulation. At the crossing point of the four electrodes, the heterodyne process for specific point stimulation produces a low frequency beat or pulse. The stimulator may be operated in any of several modes. First, constant stimulation may be applied at fixed frequency difference between electrodes. Second, the frequency difference can be decreased abruptly and returned to the original frequency difference over about 1 second. Third, the frequency difference can be decreased abruptly about 50% and returned over a typically 8 second period. Fourth, a gradual about 50% drop in frequency difference may be accomplished gradually and returned over typically a 10 second period. This device has been found to be useful in reducing pain, and appears to provide benefits in reducing edema and inflammation, increasing blood flow and reducing muscle spasms.

Each of the above devices or methods has one or more undesirable effects or deficiencies that the disclosed invention solves.

SUMMARY OF THE INVENTION

An electro-therapy apparatus and method for providing therapeutic electric current to a treatment site of a patient, having means for providing two oscillating or pulsing electric alternating currents, of frequencies which differ from each other by as little as 1 Hz and up to about 250 Hz, but each being of frequency at least about 1 KHz. The apparatus and method requires only one feed electrode adapted to feed the electric currents to selected feed sites on or beneath the epidermal or mucous surface of the patient opposite the source of pain, and only one return electrode adapted to be positioned on or beneath the epidermal or mucous surface of the patient, directly over or next to the source of pain.

The method of electro therapy includes providing a generator that generates two oscillating or pulsing electric alternating currents, of frequencies which differ from each other by as little as 1 Hz and up to about 250 Hz, but each being of frequency at least about 1 KHz. The method also includes providing a single feed electrode and a return electrode placed on or beneath the epidermal or muscular surface of a patient coupled to the generator feeding via the feed electrode two or more oscillating or complex morphology electric currents to a patient, with respective selected feed sites placed opposite one another on the patient's body with a pain site located on a line vector in between the electrode pads with the line vector perpendicular to each skin surface on which the pads reside, the currents each being of frequency at least about 1 KHz and differing as little as 1 Hz from each other by up to about 250 Hz. A non-linear action of nerve fiber membranes causes a mixing of the two independent high frequency signals in a volume of tissue surrounding and beneath a pain site pad along an axis between a pain site pad and an opposite pad to produce a therapeutic effect. The mixing yields a distribution of synthesized sum and difference frequencies among which is a therapeutic low frequency equivalent to a beat frequency of the signals.

A feedback control system for patient electro therapy includes a generator for outputting a pair of therapeutic currents feeding a single feed electrode and a return electrode. A measurement subsystem determines an impedance of the patient and a control mechanism controlling an output level of said generator.

A computer program product with an electro therapy device, includes a computer usable medium having computer readable program code means embodied in the medium for controlling the electro therapy device. The computer program product having computer readable program code means for causing a computer to control the generation of a pair of signals; computer readable program code means for causing said computer to maintain a preset frequency difference said signals; computer readable program code means for causing said computer to control an amplitude of said signals; computer readable program code means for causing said computer to detect a changed impedance of an output of said device and computer readable program code means for causing said computer change an output of said device to maintain a preset output with changing impedance of a connected patient.

Electro-therapy electrodes for providing therapeutic electric current to a treatment site of a patient are coupled to a generator providing two oscillating or pulsing electric alternating currents, of frequencies which differ from each other by as little as 1 Hz and up to about 250 Hz, but each being of frequency at least about 1 KHz. The electrodes include only one feed electrode adapted to feed said electric currents to selected feed sites on or beneath the epidermal or mucous membrane surface of the patient and a return electrode adapted to be positioned on or beneath the epidermal or mucous surface of the patient, locally to said treatment site.

BRIEF DESCRIPTION OF THE DRAWINGS

FIG. 6 illustrates an output portion of an electro-therapeutic apparatus;

DETAILED DESCRIPTION OF THE INVENTION

Description of Electrotherapeutic Apparatus Function

Figure 3:
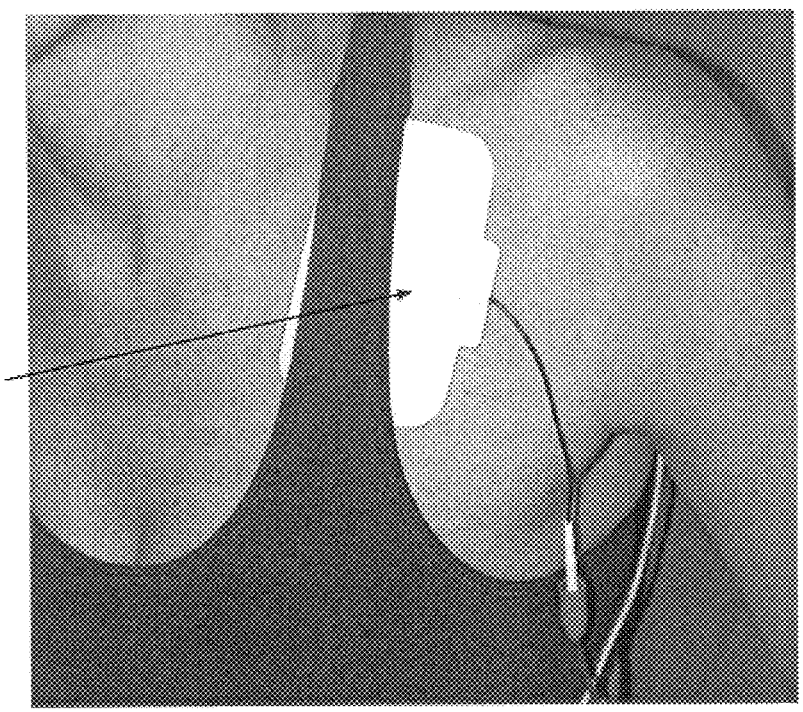
FIG. 3 illustrates an opposite pad placement for shoulder pain.
Figure 4:
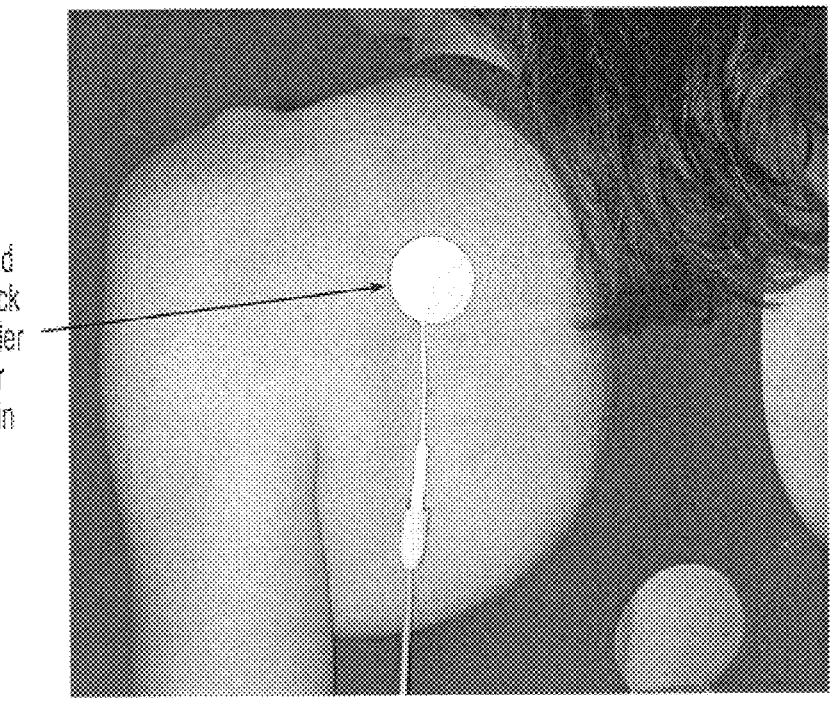
FIG. 4 illustrates a pain site pad placement for shoulder pain.

Unlike other available methods discussed above, the embodiment disclosed introduces two high frequency electronic wave-forms ("Feed Signals") into the body non-invasively through a single proprietary disposable pad placed on the skin opposite the pain site ("Opposite Pad") as shown in FIG. 3. The Feed Signals pass through the body to a second proprietary disposable pad at the treatment site ("Pain Site Pad") as shown in FIG. 4.

The Feed Signals are exponentially multiplied by materials within the body giving rise to a low frequency component, the beat frequency, in the form of an electric field within the volume of tissue defined by the geometry of the body between the electrodes. The size of the volume of tissue affected can be changed and is dependent upon electrode placement, geometry and materials, as well as the amplitude of the Feed Signal.

The two electrode pads are placed opposite one another on the patient's body with the pain site located on a line vector in between the electrode pads. Prior electrotherapy technology applications require placement of the electrode pads (typically two or more) adjacent and in the same plane as the pain site but not in an opposing placement. The ratio of the area of the pad sizes used in conjunction with one another is important in the shaping of the electric field gradient and in determining the current density through the target volume. The ratio of the area of the Opposite Pad to the area of the Pain Site Pad must be at least 2:1. The pad size ratio depends upon the application and location of the pads on the body.

The application of physiologically high frequency Feed Signals (1 kHz–100 kHz), introduced through spatially opposed electrodes gives rise to a spectrum of frequencies as a consequence of the nonlinear operations performed by polarized structures, for example nerve membranes, along the path between the electrodes, within the volume of tissue around and beneath the treatment site. This nonlinear operation yields both sum and difference frequencies from the two original Feed Signals. One of the frequencies generated, the difference between the Feed Signals, is called the Beat Frequency and is within the range (1 Hz–250 Hz) that has been determined to have a therapeutic effect with respect to pain suppression, pain management and range of motion.

Mechanisms of Action

Figure 1:
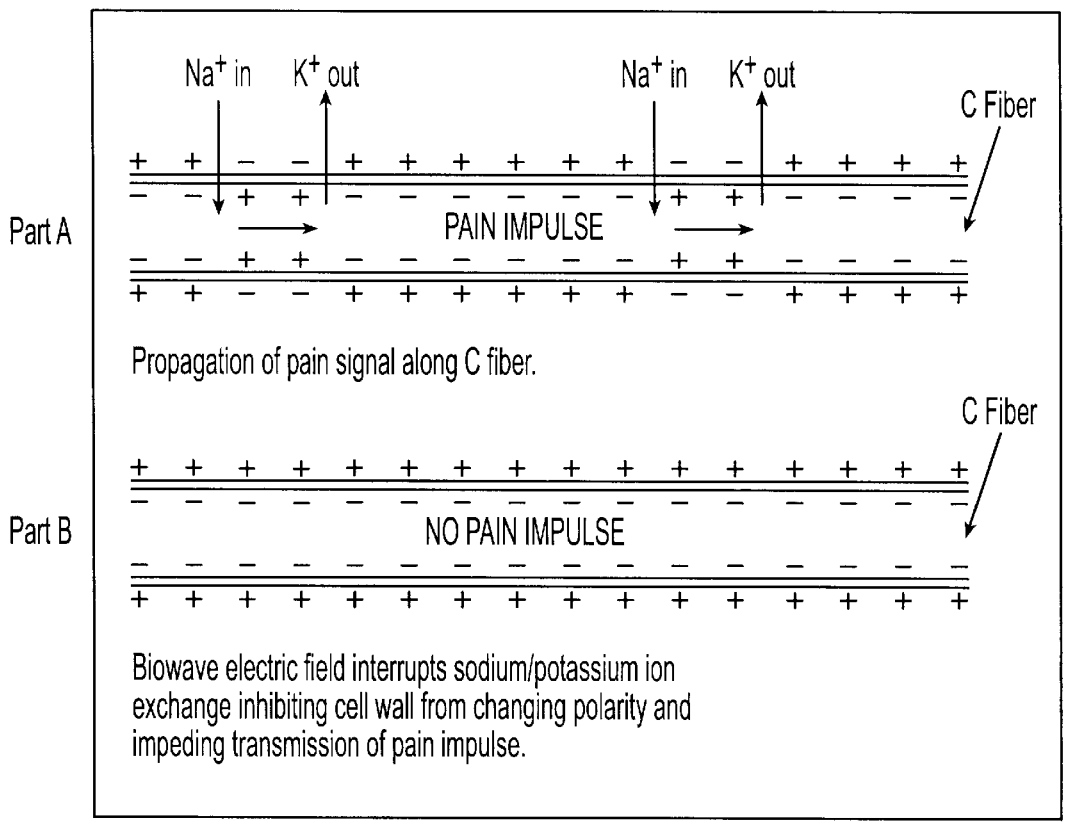
FIGS. 1A and 1B illustrate the hyperpolarization mechanism of pain reduction.

The inventors have discovered and developed a novel way to electronically block pain in the body non-invasively. Pain signals from receptors that are large enough to exceed the trigger threshold for the exchange of sodium and potassium ions across a nerve cell membrane do so through changes in the ion permeability of this membrane. This ion exchange causes a polarity change across and along the cell wall of the nerve fiber affecting the transmission of pain information along certain C type fibers as shown in Part A of FIG. 1. The inventors believe that there are several mechanisms of action caused by the Beat Frequency to reduce pain, namely (1) Frequency Conduction Block (also called Hyperpolarization), (2) Gate Control, (3) increased blood flow and (4) the release of endorphins or other opiate-like analogs.

Frequency Conduction Block. In Part B of FIG. 1, with the low frequency electric field in place, the membranes of C fibers that fall within the electric field are hyperpolarized. As a result, the sodium/potassium ion exchange is inhibited and the cell wall is prevented from changing polarity (from a negative potential to a positive potential) thus impeding the transmission of action potentials. As a result, pain impulses along the C fibers are blocked—similar in action to local chemical anesthesia, except without any deleterious side effects.

A further explanation of the therapeutic Hyperpolarization mechanism is that the resulting beat frequency, its signal morphology and current densities within the volume of tissue around and below the return electrode, causes an alteration in the nerve cell membrane's sodium/potassium ion concentrations or ion exchange kinetics. As a result, the charge polarity of the nerve cell wall is prevented from changing and is therefore unable to transmit pain impulses.

Empirically, the difference signal does not affect the sensory fibers, however, after a prolonged period of exposure to the difference signal and/or after exposure to the difference signal at high amplitudes, some sensory anesthesia can be achieved. Generally though, the resulting difference signal does not affect the transmission of touch, vibration, pressure or location awareness (proprioception). As a result, while the pain signal is blocked, patients still have sensory awareness and little numbness.

Figure 2:
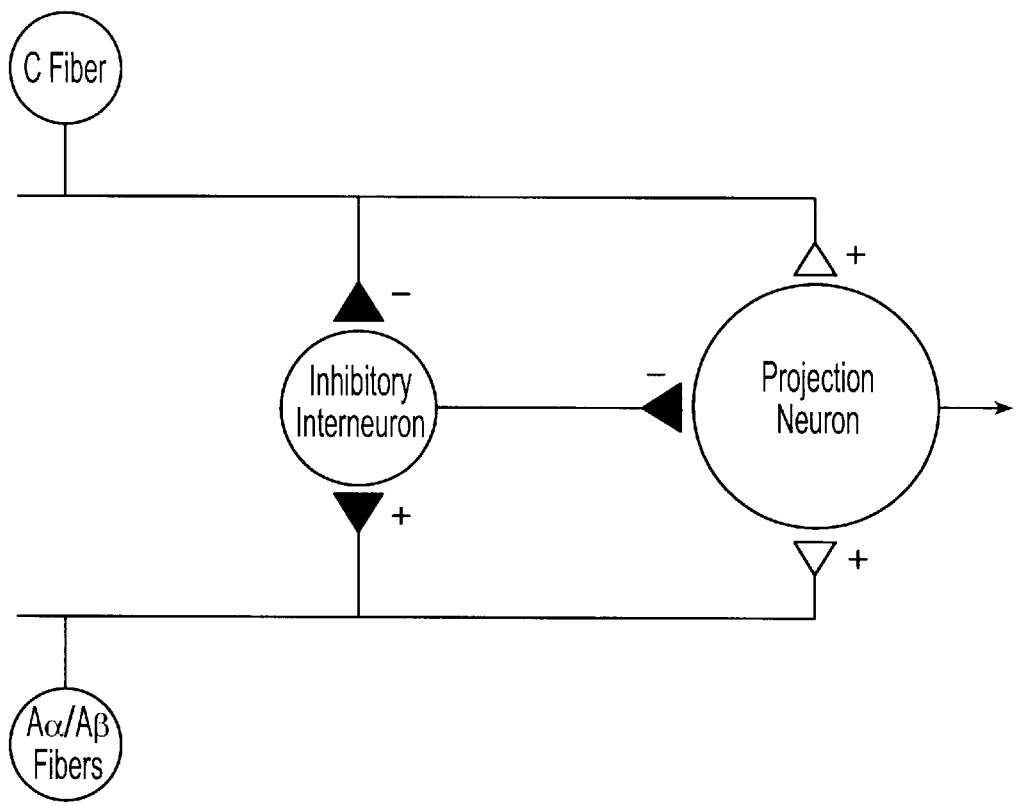
FIG. 2 illustrates the gate control mechanism of pain reduction.

Gate Control. Gate Control focuses on interactions of four classes of neurons in the dorsal horn of the spinal cord as shown in FIG. 2: (1) C fibers which are unmyelinated, (2) A□/A□ fibers which are myelinated, (3) projection neurons whose activity results in the transmission of pain information, and (4) inhibitory interneurons which inhibit the projection neuron, thus reducing the transmission of pain information.

The projection neuron is directly activated by both A□/A□ and C fibers. However, only the A□/A□ fibers activate the inhibitory interneuron. Thus when A□/A□ fibers are stimulated by the beat frequency from the electric field, the inhibitory interneuron is activated and prevents the projection neuron from transmitting pain information to the brain. The C fiber is left in a state analogous to an open electrical circuit so that transmission of the sensation of pain is suppressed.

Increased Blood Flow. An additional mechanism of action is that the resulting low frequency currents passing to the Pain Site Pad cause the formation of an electrical field that can accelerate any charged species under its influence. This may lead to an increase in local blood flow. Medical studies have shown that proper blood flow is required for the healing of any wound or injury. With the treatment application of the apparatus, there appears to be a concomitant increase in blood flow in the volume of tissue where the electric field is present that accelerates healing. Clinical evidence shows there is also a concomitant increase in range of motion for up to 24 hours following the treatment.

Release of Endorphins or Other Opiate-like Analogs. Empirical evidence suggests that residual pain relief and an increase in range of motion can last for up to 24 hours following a twenty (20) minute treatment. The residual effect involves either a refractory mechanism involving the membrane itself or the local release of endorphins, enkaphlins or other opiate-like analogs.

Primary Residual and Secondary Residual Effects

In the preferred embodiment of the electrotherapeutic apparatus, a series of sinusoidal Feed Signals are generated and applied either individually or electronically summed to a patient via a single feed electrode. These Feed Signals or signal appear at the return electrode as a series of signals representing the sum, difference and original input frequencies. The potential difference between the inside and outside of a nerve membrane is around −75 millivolts. Due to the potential difference and differences in ion mobility, activity and half-cell electrical potential, a nerve cell membrane can be modeled as a weakly rectifying junction. Weakly is used to describe the nerve cell membrane's performance because of large deviations in its behavior from an ideal diode. Deviations in the nerve cell membrane's behavior arise due to shunt capacitance and leakage conductivity arising from membrane's aqueous ion environment. The membrane is still capable of exponential response to an electrical signal. As a result the membrane acts as a device causing mixing of the Feed Signals, and yields a distribution of synthesized sum and difference frequencies among which is a therapeutic low frequency equivalent to a beat frequency of the Feed Signals.

The Feed Signals, that are generated by the oscillators in the electrotherapeutic apparatus, form within the body, a complex combination of the sum and differences of such signals. The sum signals are at a frequency far from the capture range or physiological effect range (physiological effect range <<1 KHz) of the nerve membranes of nerve fibers that control pain signal transmission. However, the difference signal (Beat Frequency signal), when the initial Feed Signal frequencies are set properly, is within the therapeutic range (1 Hz to 250 Hz.) and interacts with nerve membranes at the rate of this low frequency beat.

Depolarization of afferent A-fibers, is believed to switch-on an inhibitory neuron that inhibits the action of a projection neuron at the dorsal horn of the spine. This effectively disconnects the pain receptors (C fibers) from the brain. This is known as the gate control mechanism and is well known and accepted by the neuroelectrophysiology community. Additionally, it is possible that the driven polarization/depolarization afforded by the electro-therapeutic apparatus saturates the nerve's ability to transmit information to the spine. The exact effect is not absolutely known. The effect of the signal on pain is the perception of numbness or dulling without loss of heat or mechanical response to external stimuli. The method has an effect that appears to last longer than the time of the application of the electrical fields. Empirical evidence suggests the Primary Residual Effect can last for up to 60 minutes before nerve membrane cells can begin changing polarity again and allow transmission of some pain signals. The Secondary Residual Effect involves either a refractory mechanism involving the membrane itself or the local release of endorphins, enkaphlins or other opiate-like analogs and empirical evidence has shown this effect to last up to 24 hours.

Multiplexing

Both Primary Residual and Secondary Residual effects described above, (which can be referred to as "flywheeling"), affords the electrotherapeutic apparatus some additional capabilities. Among these capabilities include large area pain control. If one properly multiplexes or switches between several feed and/or return electrodes at a rate of 10–50 Hz, the flywheel effect will fill in the gap when a particular area is not under the influence of the electric field. This proper multiplexing includes the timing corresponding to the zero crossing of the sine wave so as not to induce spikes in the signals due to abrupt current collapse in the output transformers or inductor-based filter network (if they are used). This allows the apparatus to synthesize a large effective area without the need for a much more complex apparatus or physically moving the electrodes which would cause the area not under the field's influence to feel sensation again.

Unique Method

The electro-therapeutic apparatus disclosed is unique in that it can mimic multi-electrode (more than two or a pair) apparatuses with much greater precision and control, and additionally and more importantly, can interrupt the transmission of a pain signal, or more generally, place an AC signal within the body using only one feed electrode and one return electrode.

In simple terms, the electro-therapeutic system is either turning off a particular pain fiber, proximal to the treatment site, or inhibiting pain signal transmission via the stimulation of inhibitory neurons that control pain transmission to the dorsal horn of the spine and brain. As is well known in the art, all pain signals travel first through the dorsal horn of the spine and then onto the brain.

Current TENS type apparatuses in use rely on either pulse operation or multiple signal application to affect nerve fibers. In TENS type apparatuses a unipolar or bipolar pulse is applied to the target area. These pulses are of short duration and can cause undesired stimulation of other tissues especially muscle. Multiple signal application requires that two or more feed (signal) electrodes be placed at different points on the body so that the resulting electric field and current can be summed at the return electrode thereby causing the desired effect. TENS type apparatuses suffer from the need for multiple electrodes and power amplifiers for each signal channel. As the number of signals increases, so do the demands on electrode placement and circuit design.

The disclosed electrotherapeutic apparatus is an "instant system" because the sinusoidal signals of the desired frequencies are electronically summed in the power amplifier stage. If desired, the signals can be individually amplified and the resulting high-level signals summed at the pad(s) through load leveling resistors. There are several advantages to the "instant system" design. There is need for only one feed electrode regardless of the number of signals to be summed. If one assumes that the relative amplitudes and in turn the signal envelope morphology is known for a given target region, a more precise control of the final field at the return electrode is afforded. This is because the path lengths and interposed electrical properties of the tissues along this path appear nearly the same to the Feed Signals. In a system with feed signals fed through multiple feed electrodes the paths can vary greatly, altering the fidelity and bioelectric characteristics of the resultant signal. For instance, current for each feed signal can differ widely due to variations in path length and the chemical/anatomical environment along such a path. Degradation of individual feed signals can also be caused by the need for multiple signal electrodes. No electrode/body interface is perfect. Each electrode attachment introduces impedance that differs from place-to-place where the attachments take place. This is due to a myriad of factors such as skin moisture/ion content, skin mechanical condition and surface shape, site prep and electrode manufacturing variability. The use of a single signal feed causes the outcome of these variables to impact all the desired signals in parallel. This effectively nullifies the problems that arise from the differential effects that arise when multiple variables impact multiple signals independently.

Feedback

The use of a single feed also reduces the computational burden and circuit complexity of a feedback mechanism that is used in the disclosed apparatus. Feedback and fuzzy logic computation enables the output of the apparatus and the resulting field to be maintained within limits that afford much greater patient comfort and in turn compliance and results in the use, on average, of the minimum signal amplitudes required for the desired effect. This differs importantly from apparatuses with no physiological (i.e. body impedance) feedback process. In these systems any instantaneous variability in impedance can cause a rapid rise in applied signal amplitude that can be extremely unpleasant to the patient. The side effect of this is the patient altering the output to eliminate the signal change and eventually, when the impedance changes again, not having the correct amplitude to cause the desired level of pain control.

Since the electro-therapeutic apparatus generates a set of sine waves or an admixture of sine waves of arbitrary frequency, its concept can be extended to generate an arbitrary waveform of any intensity and harmonic content. The arbitrary waveform generation (see also discussion of direct digital synthesis) is a consequence of the Fourier series where a subset of a basis set of sine waves can be algebraically summed to generate any waveform. This technique can be used to tailor a pulse that can be useful in pacemaker or cardioverting applications.

Studies have shown that variations in patient posture and blood flow can alter the impedance seen by the device. These impedance changes can cause the voltage of the applied signal to increase. This effect is due to the non-ideal output regulation of the device. Some patients perceive this instantaneous increase in applied voltage as an unpleasant sensation. In order to insure patient compliance with the proper use of the device it is necessary that some form of feedback be employed to insure that the applied signal levels are appropriate for a given load. The feedback network consists of two functional parts: 1) a circuit (Hardware), that monitors the patient-applied current and voltage and 2) software that determines if the values measured require an output level change (Software). The parameter derived from the current and voltage is the impedance across the patient-applied electrodes. This parameter has been found by studies to be essentially invariant at a particular frequency (frequency interval for this device) and over the range of applied potentials used clinically. Further, any impedance change due to a change in patient position essentially disappears when he or she either returns to the position held before the impedance change or after there is a equilibration of blood flow.

Additional Features

In the preferred embodiment of the electrotherapeutic apparatus, the Feed Signals are summed at a low level before the power amplifier. An alternative would be to send each Feed Signal separately from the output(s) of the power amplifier(s) and cause them to be mixed at the pad itself.

The electrotherapeutic apparatus allows the amplitude of the Feed Signals to be adjustable and controlled by the patient so that treatment level and comfort can be customized to each individual patient.

The electrotherapeutic apparatus also has an optional automatic mode setting that memorizes the amplitude settings of the Feed Signals during the course of the entire treatment. The apparatus stores this information in memory for a given treatment location and creates an auto Feed Signal profile for the patient. The patient then has the option during future treatments to run the electrotherapeutic apparatus in an automatic mode so that they do not have to manually increase the amplitude of the Feed Signals. The auto profile would be updated with each new set of data points that were manually generated.

The pads that connect the instrument to the body are of a certain conductive material that allows propagation of the physiologically high frequency signal. The connection between the lead wire and the electrodes is of a unique low profile design that allows for easy connection and comfortable use under clothing.

Circuit Description—Method 1

Figure 5:
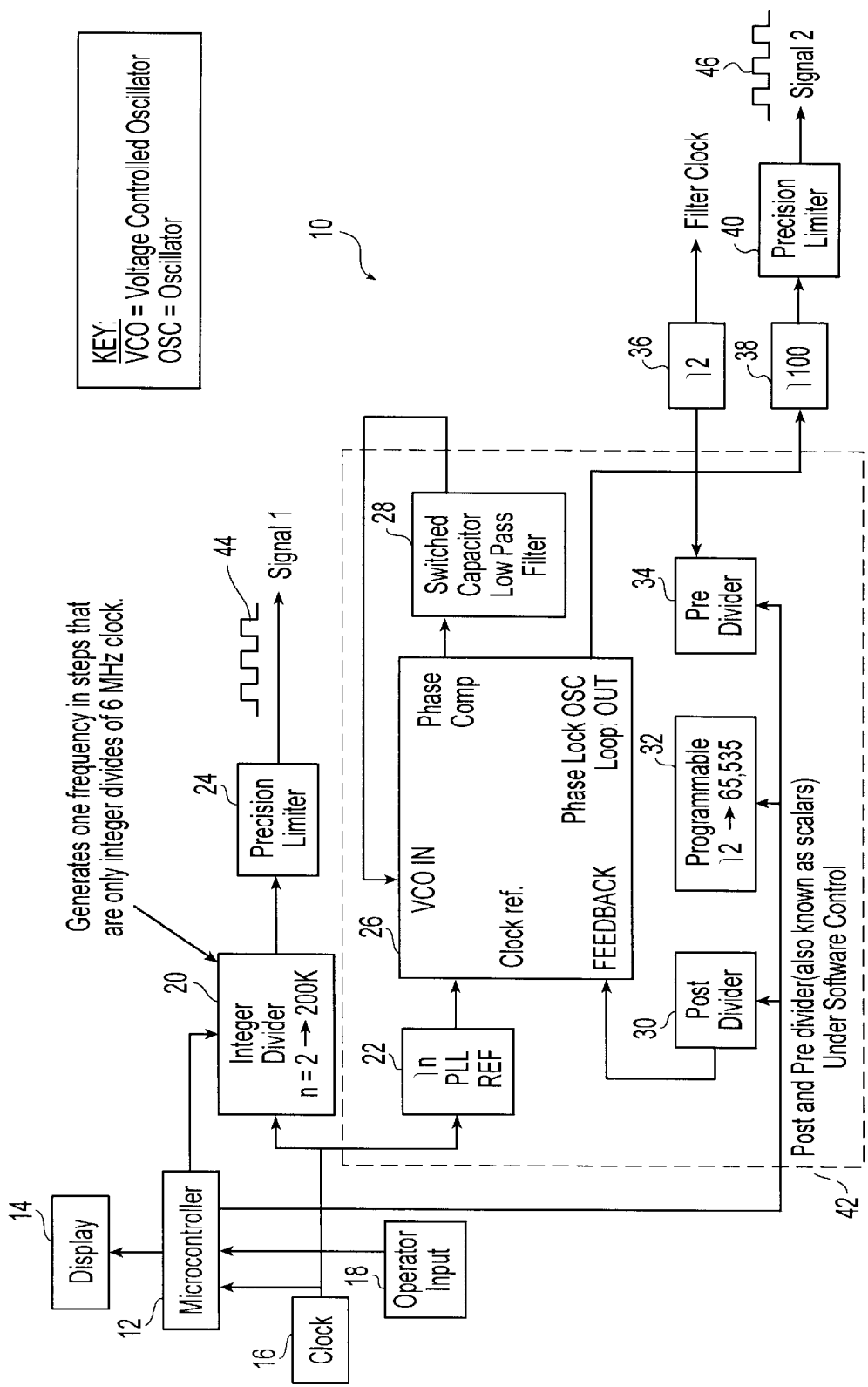
FIG. 5 illustrates a frequency generation portion of an electro-therapeutical device.

The electro-therapeutic apparatus can be useful in any situation where either an AC field, within a physiologically active frequency range, is needed (pacemakers, part of pain control, local healing, bone growth, cartilage regeneration) or where information transmission, i.e. sensory prosthetics, would be useful (vision, sound, touch). FIGS. 5–9 illustrate the structure of an electro-therapeutic apparatus (Apparatus) as discussed above. FIG. 5 illustrates the control and generation of the frequencies used in the Apparatus. A high integration micro controller 12 supervises the entire operation of the apparatus. The microcontroller 12 is responsible for interpreting operator commands and for displaying system status on the LCD display panel 14. Additionally, the processor controls the frequencies of the signal sources, their levels and compensates for any variation in system load. This last function is important since changes in patient electric load can affect the signal level and the perceived sensation of the apparatus effect. The micro controller uses feedback to control signal levels by comparing the immediate electrical load to previously "learned" characteristic rules for a particular patient. The micro controller receives a clock signal from a clock generator 16. In addition the micro controller 12 receives operator instructions from an Operator Keypad 18. As discussed above and shown in FIG. 6, the micro controller provides instructions to various portions of the signal generation system. The signal system generates two signals, signal 1 44 and signal 2 46.

The reference frequency for the synthesis of the signals ultimately applied to the patient is derived from the micro controller clock 16. This clock source is a crystal oscillator with an error of 50 ppm and slow aging characteristics. An exemplary clock frequency is 6 mHz. In a two signal system (these methods are easily extended to multiple signals) one frequency is fixed to the output of a divider chain 20 of the system clock 16. The clock 16 is coupled to the input of the divider chain 20. The derived frequency can be set anywhere within the apparatus's exemplary operation frequency range of 1 Hz to 150 KHz. The output of divider 20 is coupled to a precision limiter 24 to generate a square wave of a limited value. The output of precision limiter 24 is designated Signal 1 44 and is coupled the output circuitry described in FIGS. 6 and 7 below.

Outputs of the clock 16 and micro controller 12 are also coupled to elements of circuitry that generates any frequency between 2 Hz and 200 KHz 42. The clock signal is coupled to a "divide by n PLL reference" block 22 that is coupled a first input a "phase lock loop block" 26. The phase lock loop 26 is controlled by two loops. The first loop comprises an output coupled to the switched capacitor 5th order DC corrected low pass filter 28 which has its output coupled to the phase locked loop 26. A second loop comprises an oscillator output of phase locked loop 26 which in turn is coupled to a combination of a pre-divider 34, a programmable divide by 2 to 65535 divider 32 and a post divider 30 each of which are coupled to an output of microprocessor 12. The output of post divider 32 is coupled to a feedback input of the phase lock loop. This subsystem 42 generates any frequency between 2 Hz and 200 Khz with a 1 Hz resolution. The Oscillator output of phase lock loop 26 is coupled to a divide by two block 36 providing a filter clock and a combination of a divide by 100 block 38 and precision limiter 40. The precision limiter 40 provides a limited signal output 46 similar to Signal 1 44. In situations where a variable range for Signal 2 is not necessary a divider system as outlined for Signal 1 can be substituted for the PLL network. This option necessitates the use of a non-standard custom crystal for the main clock so that the proper frequency separation can be maintained.

Circuit Description—Method 2

The second method used to develop an arbitrary waveform morphology involves the method of Direct-Digital-Synthesis (DDS). With this subsystem the above phase-locked-loop, frequency divider and filter sections discussed below, are not used. The DDS instead involves downloading to the Apparatus a binary representation of the desired waveform from a host computer that calculates these coefficients as a table. These values transferred to the Apparatus's memory space are saved in EEPROM and are used as a lookup table to drive, at a rate determined by a micro controller derived clock a high-speed precision digital-analog controller (DAC). The DAC converts the calculated values into analog form (either voltage or current) that is subsequently low-pass filtered to eliminate any high frequency content in the synthesized signal. This high frequency content is a consequence of the discrete nature of the reconstructed signal. The output of the DDS system is a low distortion representation of an arbitrary waveform. The DDS is used in any embodiment of the apparatus where a limited number of sine's or cosines will not adequately lead to the formation of the desired signal morphology.

Figure 6A:
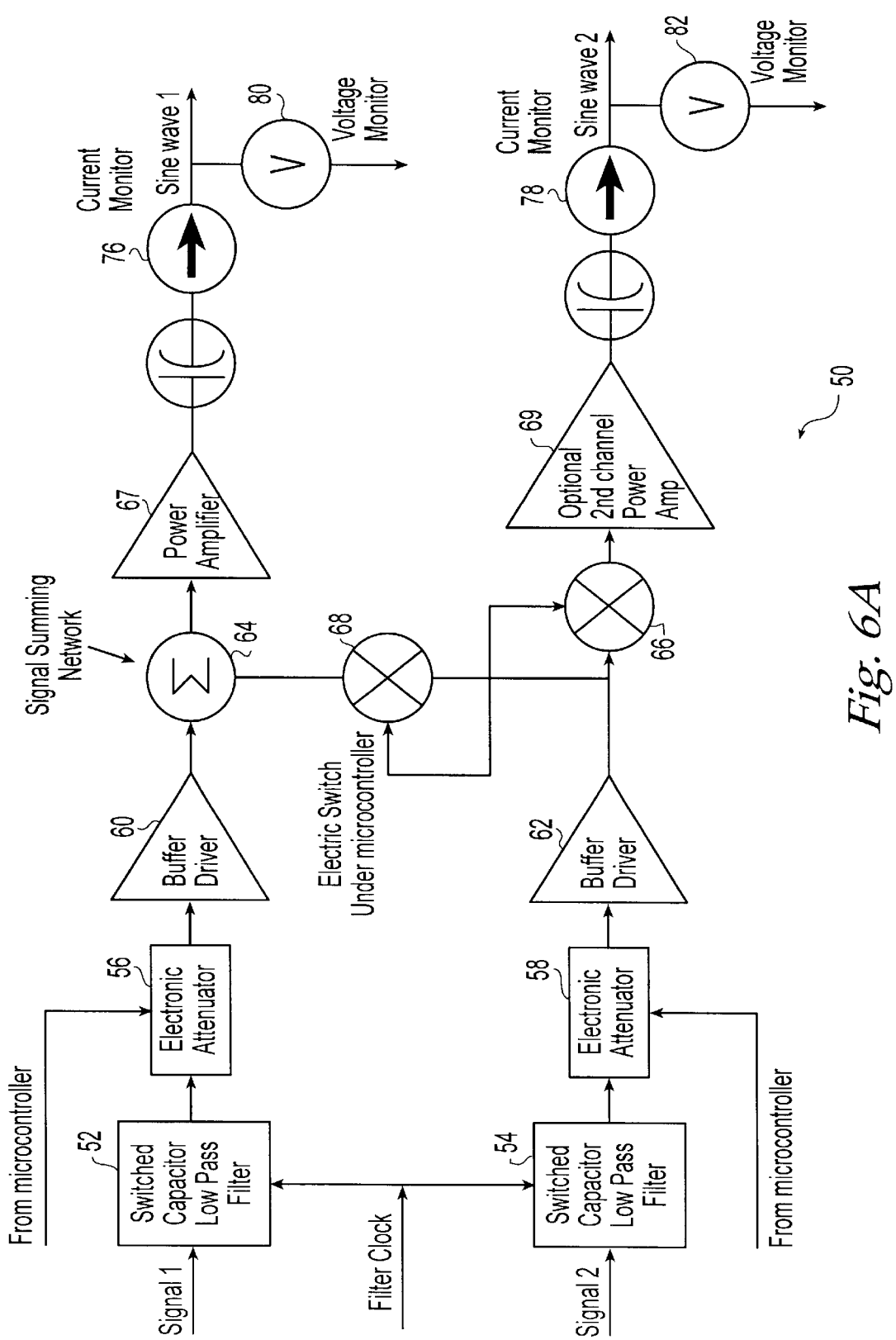
FIGS. 6A & 6B illustrate output portions of an electro-therapeutical device.

FIG. 6A illustrates a sub-system for convening Signal 1 and Signal 2 to sine wave signals. As discussed above the ultimate output signals of an electrotherapy need to be as close to a pure sine wave as possible. Signal 1 and Signal 2 are initially logic level square-type waves. These signals are limited to 0.6V amplitude by the transistor limiters 24 and 40 shown in FIG. 5. The outputs of these limiters are applied independently to high order low pass filters (switched capacitor type 2nd or 8th order depending on required signal distortion levels) 52 and 54. The filter clock output of "divider by 2" 36 is coupled to each of the filters. These filters suppress the higher order harmonics present in the limited square waves leaving a low distortion sine wave at the reference frequencies. These sinusoidal signals are amplified and applied to electronic attenuators or programmable amplifiers 56 and 58 (under microprocessor 12 control) to control the level of the signal applied to the power amp stage, discussed below, and ultimately to the patient.

Figure 7:
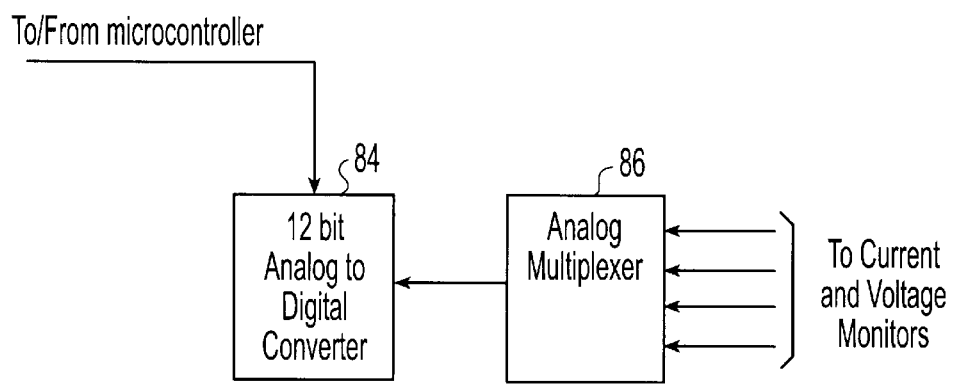
FIG. 7 illustrates a sub-system portion of an electro-therapeutic apparatus.

FIG. 7 illustrates a sub-system for converting Signal 1 and Signal 2 to sine wave signals. As discussed above the ultimate output signals of an electrotherapy need to be a close to a pure sine wave as possible. Signal 1 and Signal 2 are initially logic level square-type waves. These signals are limited to 0.6V amplitude by the transistor limiters 24 and 40 shown in FIG. 5. The outputs of these limiters are applied independently to high order low pass filters (switched capacitor type $2^{nd}$ or $8^{th}$ order depending on required signal distortion levels) 52 and 54. The filter clock output of "divider by 2" 36 is coupled to each of the filters. These filters suppress the higher order harmonics present in the limited square waves leaving a low distortion sine wave at the reference frequencies. These sinusoidal signals are amplified and applied to electronic attenuators or programmable amplifiers 56 and 58 (under microprocessor 12 control) to control the level of the signal applied to the power amp stage, discussed below, and ultimately to the patient.

Figure 6B:
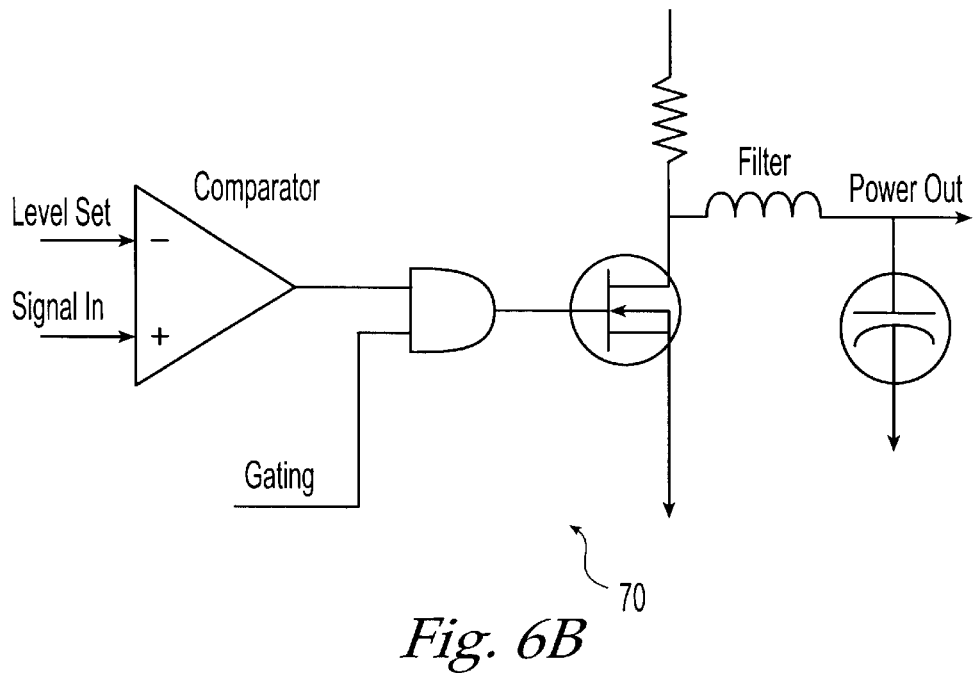

The signals from above are buffered 60 and 62 and applied to a power gain stage. The power stage consists of one or more amplifiers 67,69 capable of supplying a wide range of voltages into any physiological and electrode load over the frequency ranges used. Depending on the desired level of system integration and/or portability required, this amplifier stage can be either of the linear Classes A or $AB_1$ or the nonlinear switching Class D type. For the linear amplifiers a high power operational amplifier is operated in either a ground-referenced mode or in a bridge configuration. In the bridge configuration the load is connected differentially to the outputs of two power amplifiers that operate 180 degrees out-of-phase with respect to one another. In either configuration the amplifier's DC offset is nulled by a servo correction amplifier. Since the amplifiers are also setup as AC coupled amplifiers essentially no DC current flows to the load. In the ground referenced mode higher output voltages are developed by passing the amplifiers output to a high efficiency transformer (s). In the bridge topology the amplifiers, when in balance, generate essentially no net DC current. Additionally, this composite amplifier can swing an output level twice that of the individual amplifiers. This, amplifier topology will, in most circumstances, eliminate the need for an output transformers) and its weight, circuit board real estate requirements and power losses. Factors very important to a small, portable and lower battery current embodiment of the Apparatus. The second class of amplifiers, which also improves performance in a portable system, is that of Class-D 70, such as seen in FIG. 6B. For this amplifier a high-speed comparator varies the pulse width of a switching power transistor (MOSFET type). This modulation is called pulse width modulation and is driven by the original signal's frequency, amplitude and desired gain. The sampling of the reference signal, derived from either the PLL reference or DDS, is sampled at a rate at least one order of magnitude higher than the highest frequency component in said reference. The output of the power transistor is lowpass filtered by a passive LC network to yield the amplified signal. The mode of amplifier operation is particularly attractive since power conversion efficiencies of over 90% can be obtained as opposed to the efficiencies of linear amplifiers that are around 40%. The micro controller sets, via electronic switching 68, whether the signals are summed at an amplifier to create the mixed signal or applied individually to the power stage and thereby allow the mixing to take place within the patient's body. Additionally, one or more channels and/or return signal paths can be multiplexed with electronic power switching during zero crossing of the sine wave signals (via processor control). This multiplexing or switching allows multiple electrodes to be fed from the amplifiers or connected to the analog return. This is done to synthesize a larger effective target region on or within the patient. The patient is electrically isolated from leakage to power mains by the isolated plastic housing of the Apparatus and by the use of a battery power supply.

To monitor and subsequently control the signals applied to the patient a set of multiplexed ammeter and voltmeter circuits 86 as illustrated in FIG. 7 are used. The rms amplitudes of the feed voltage and current for each channel are digitized 84 (as illustrated in FIG. 7) and read by the micro controller 12. This enables the processor to measure dynamically the load impedance, delivered power and, in the case of multiplexed electrode sites, energy applied to the patient. All of these parameters along with system state (i. e. electrode configuration, frequencies, battery condition and amplifier configuration) are continuously available via an RS-232 port. This serial port can be connected to a PC and these data logged for later analysis (other communication protocols can be easily substituted for RS-232 such as USB or Firewire). The information derived as to patient impedance load or power delivered is compared by the microprocessor to reference values taken during system setup. This comparison allows the system to vary the amplitude of the output signals to eliminate any load induced variations in the perceived signal levels thereby affording greater patient comfort.

Figure 8:
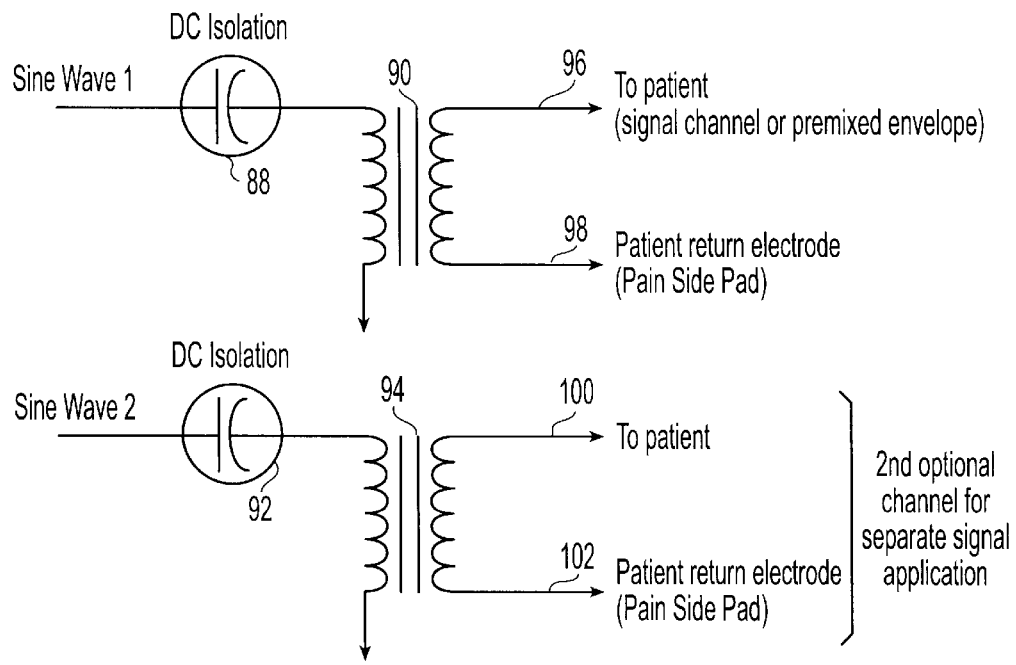
FIG. 8 illustrates coupling of outputs of an electro-therapeutic apparatus to one or more electrodes.

FIG. 8 illustrates the coupling of Sine wave 1 and Sine wave 2 to the electrodes when the apparatus is constructed around ground reference (local Apparatus ground) linear power amplifiers. The sine wave signal is coupled from the junction of current monitor 76 or 78 and voltage monitor 80 or 82 to a DC isolation capacitor 88 or 92. This capacitor removes any remaining DC component on the sine wave signal. The sine wave signal is coupled to transformer 90 or 94. The output of the transformer 90 is coupled to the patient electrodes. One output of each transformer 96 or 100 is coupled to a large signal electrode and the other to a small return electrode 98 or 102. The transformer provides voltage gain and patient/apparatus isolation. With bridged amplifiers or in Class D operation no such transformers are required. As discussed above, the Opposite Pad electrode has a much larger surface area contacting the patient than the Pain Site Pad return electrode. This size ratio of the Opposite Pad electrode to the Pain Site Pad electrode is at least 2:1.

Figure 10:
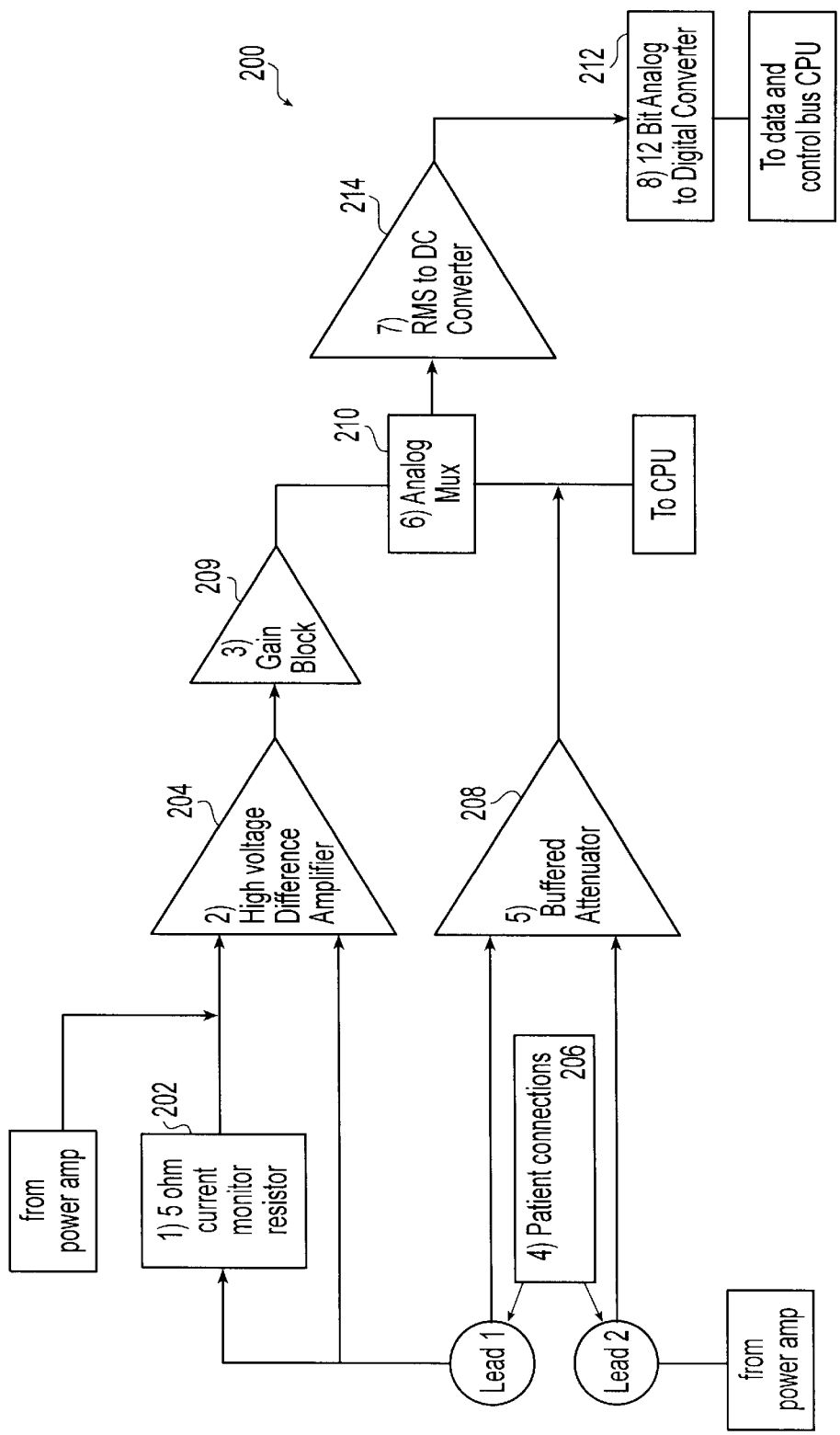
FIG. 10 illustrates a block diagram of a feedback system for controlling the output of the electro-therapeutical device.

Feedback Hardware:

A feedback system is illustrated in FIG. 10 as 200. The current level through the patient is monitored by a precision 5 ohm resistor 202. A voltage is developed by the current through this resistor and is differentially detected by an amplifier 204. This signal level is further amplified by gain block 209. Coincident with this measurement the voltage across the electrodes 206 is sampled by a buffered attenuator 208 to set its value to within the range of the Analog-to-Digital (ADC) circuit. An analog multiplexer 210 is used to select either the current or voltage representations for digitization. This selection is under the control of the CPU. The output of the multiplexer is applied to a precision RMS to DC converter 212 whose output is a DC level approximately equal to the RMS value of the applied signal. The output from 212 is digitized to 12 bits by the ADC 214 and passed to the CPU. The same digital attenuator that is used to set the output level from the patient adjustable control makes any changes to the output level that might be required by the feedback subsystem.

Software

Figure 11:
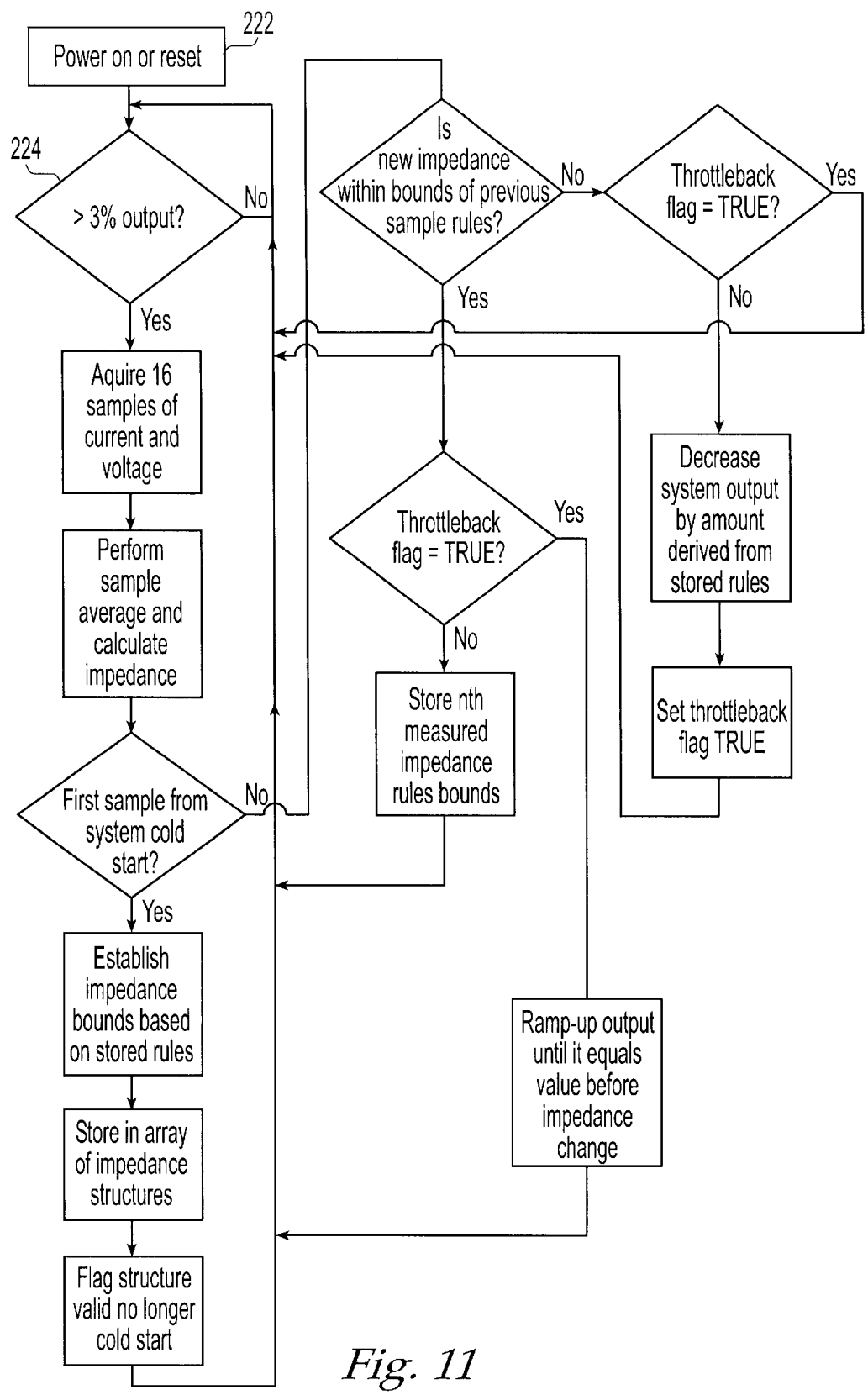
FIG. 11 illustrates a software flow diagram of a feedback system for controlling the output of electro-therapeutical device.

The second section of the feedback control network is the software controller 220. This collection of routines determines if the measured impedances require any change to the device's output level to maintain patient comfort. The flow chart in FIG. 11 outlines the logic of the software function. On power up or hard reset 222 the software waits until the output level is of sufficient amplitude (about 3% of full power) 224 to assure accurate measurement of the voltage and current across and through the patient. When this level is achieved the software collects 16 samples of both the current and voltage 224 and performs an averaging of the derived impedances. Previous experiments have helped to define a set of rules as to what ranges of impedance variability can be expected when the patient load can cause an alteration of applied field that can cause an unpleasant sensation for the patient. Additionally, the rules encompass the range of impedance values that can be expected when the patient load tends toward that initially encountered. These rules are used to predict what impedance range can be expected when the device output is altered via the patient adjustable control. If the impedance value is not within those set by the rules the output is reduced by an amount dictated by another set of rules derived for the particular output level currently being used. The effect is a reduction in the applied field and the elimination of any unpleasant sensations. If the impedance values at this new field level trend back to within the stored"normal"range the output is restored to its value held previous to the impedance change. The rate at which this takes place is set by another set of rules that are derived as a function of the absolute difference between the desired output and the feedback-set output. This assures that the device effect on the patient is restored as quickly as possible with little perception, by the patient, of the increasing field. If the impedance never achieves the values set by the originally derived rules the patient is informed that the electrodes and/or their interfaces with the body have been compromised. If the electrodes appear correct or if there are no unpleasant side effects accompanying the impedance change the patient can tell the system to use the new impedance values to derive a new set of rules to govern device operation. However, if no action is taken within a prescribed period of time the device will automatically shutdown the output amplifier and signal an error on the display. FIG. 11 details the progress of the software system determining the impedance levels within the patient and shutting down the system or maintaining a proper output level depending upon the impedance of the patient. This includes establishing impedance bounds as well measuring over numerous measurements and determining an average impedance.

Figure 9:
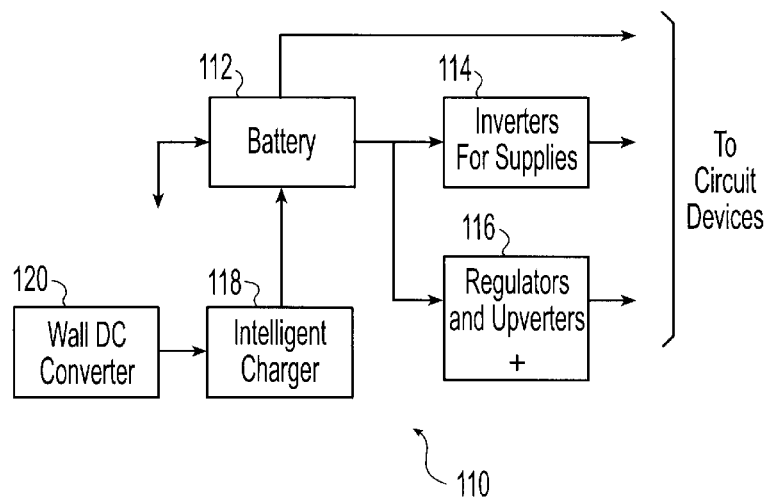
FIG. 9 illustrates the power system of an electro-therapeutic apparatus.

FIG. 9 depicts a power supply 110 for the present invention. Two 12-volt batteries in series are currently used to supply differential input power 112 for the system. The 7-volt feed is developed by a high efficiency step-down switching regulator and is used to supply linear regulators 116 that power low voltage subsystems such as the micro controller and low voltage analog components. The 12 volts is also inverted by inverters 114 and regulated to supply the negative low voltage used by some analog components. The 12-volt supply is used directly for some higher voltage analog components and is also stepped up and/or inverted to supply up to +/−50 volts for the power stage. The battery pack is recharged by a DC wall pack supply 120 that supplies a switching-type recharging circuit 118. Additionally, the apparatus can be operated and/or recharged by connecting a cable between the Apparatus and the accessory connector within a car, boat or plane. Battery state is monitored, during apparatus operation, by an analog-to-digital converter that is polled by the micro controller from time-to-time. This value is indicated as a battery bar graph on the display panel. If for some reason the voltage level drops below a useful level the micro controller automatically generates a global reset effectively shutting down the system thereby turning off the output signals.

Ambulatory Design

Many applications of electro-therapy require portability. Treatments are more efficiently administered by a wearable apparatus, preferably hand held or attached to the belt or other location on the body. The design of the apparatus is such that one embodiment of the apparatus is easily packaged in an apparatus that the patient can use in a wearable/portable manner. Such applications for an ambulatory apparatus include use while walking, working, sitting at a desk; use at home, while watching TV, sitting in a car, or in a manner prescribed by the physician. The programming capability permits the company or the physician to program the portable apparatus to fit the patient's needs. This may include an elapsed timer within the apparatus, to limit the patient's use if that is desirable from a medical point of view.

Empirical Results

In addition to pain relief, other significant effects resulting from the generation of a low frequency electric field in deep tissue are increased blood flow in the volume of tissue where the electric field is present as well as an increase in opiate like analogs such as endorphins, serotonin and enkaphlins. Empirical results from clinical trials suggest that either hyperpolarization of nerve cells or gate control is the likely mechanism of action for pain relief while the apparatus is on and the electric field is present. Increases in range of motion are believed to be a consequence of increased blood flow at the joint or source of pain. The residual effect of both pain relief and increased range of motion are possibly due to an increase in the concentrations of aforementioned opiate analogs. Additionally, at excitation frequencies above 4 Hz (sinusoidal), muscle tension holds at a fixed level. This tension acts to hold a muscle in stretch thereby possibly conditioning it. This effect is similar to isometric exercise where a fixed load is presented to a muscle group held in place. This effect also helps explain why the current embodiment of the invention causes little or no uncomfortable muscle twitch as seen with pulse-type (TENS) devices. It is quite likely that some combination of these three mechanisms all produce the efficacious results acquired in clinical studies.

Figure 12:
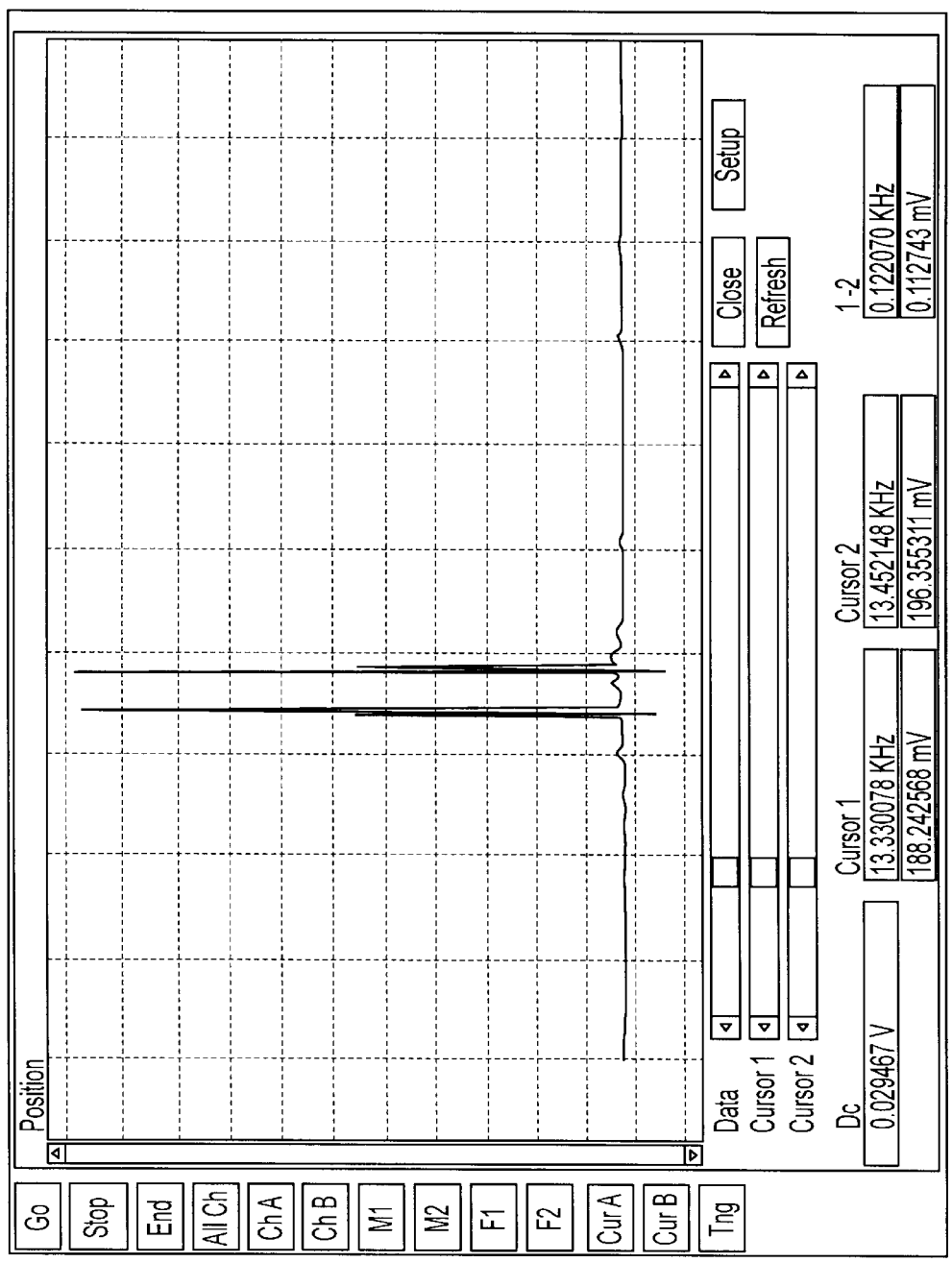
FIG. 12 illustrates a waveform representing the current flow form the device.
Figure 13:
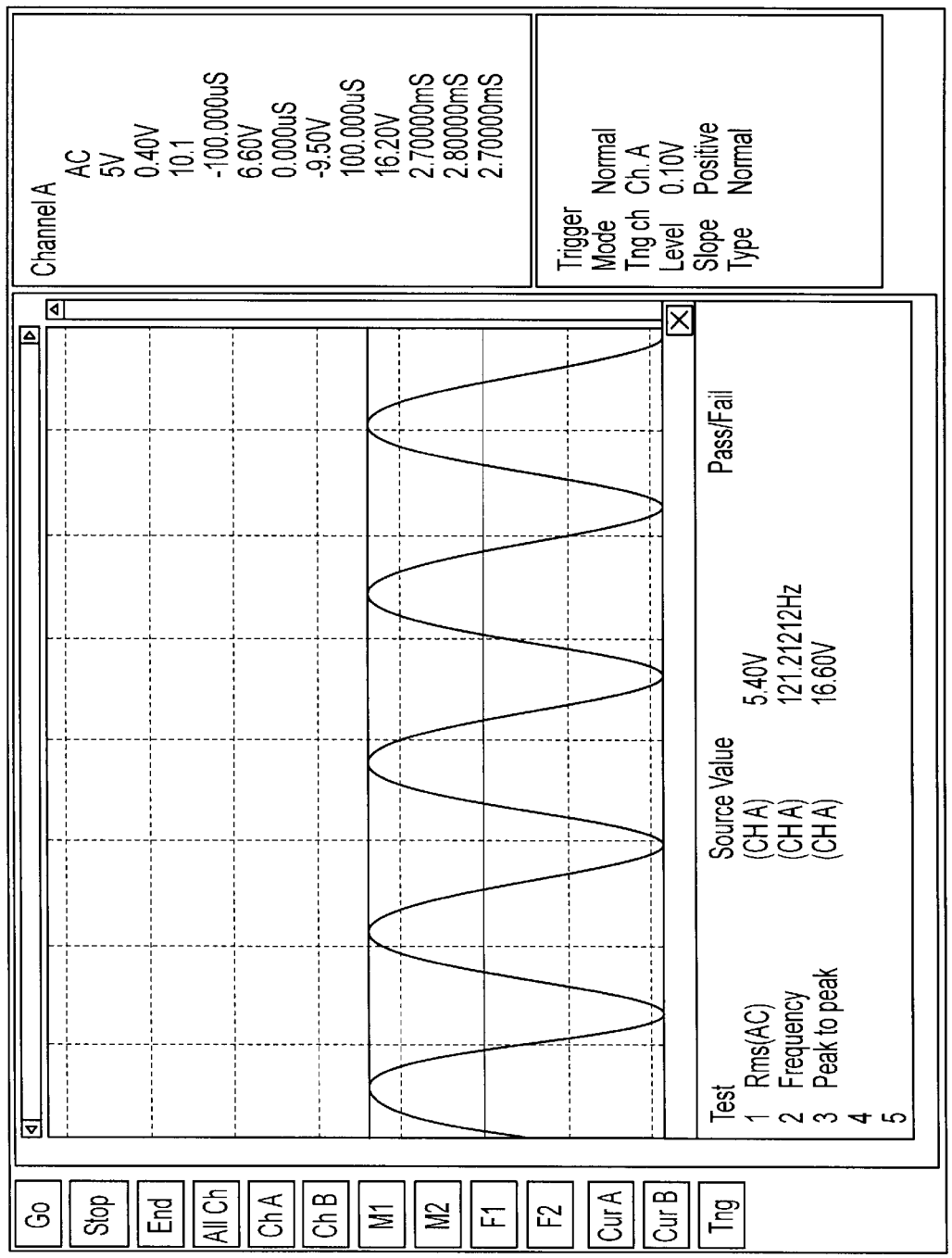
FIG. 13 illustrates a waveform of the morphology of the effective signal.

FIGS. 12–15 are various waveforms illustrating features of the device. FIG. 12 illustrates a waveform representing the current flow form the device in a simple dual sine wave mode into a 1.2K ohm resistive load. FIG. 13 illustrates a waveform of the a recording of the mixed signal after it is passed through a high speed filter, followed by a 1 $\mu$fd. capacitor acting as a filter. This simulates the morphology of the effective signal.

Figure 14:
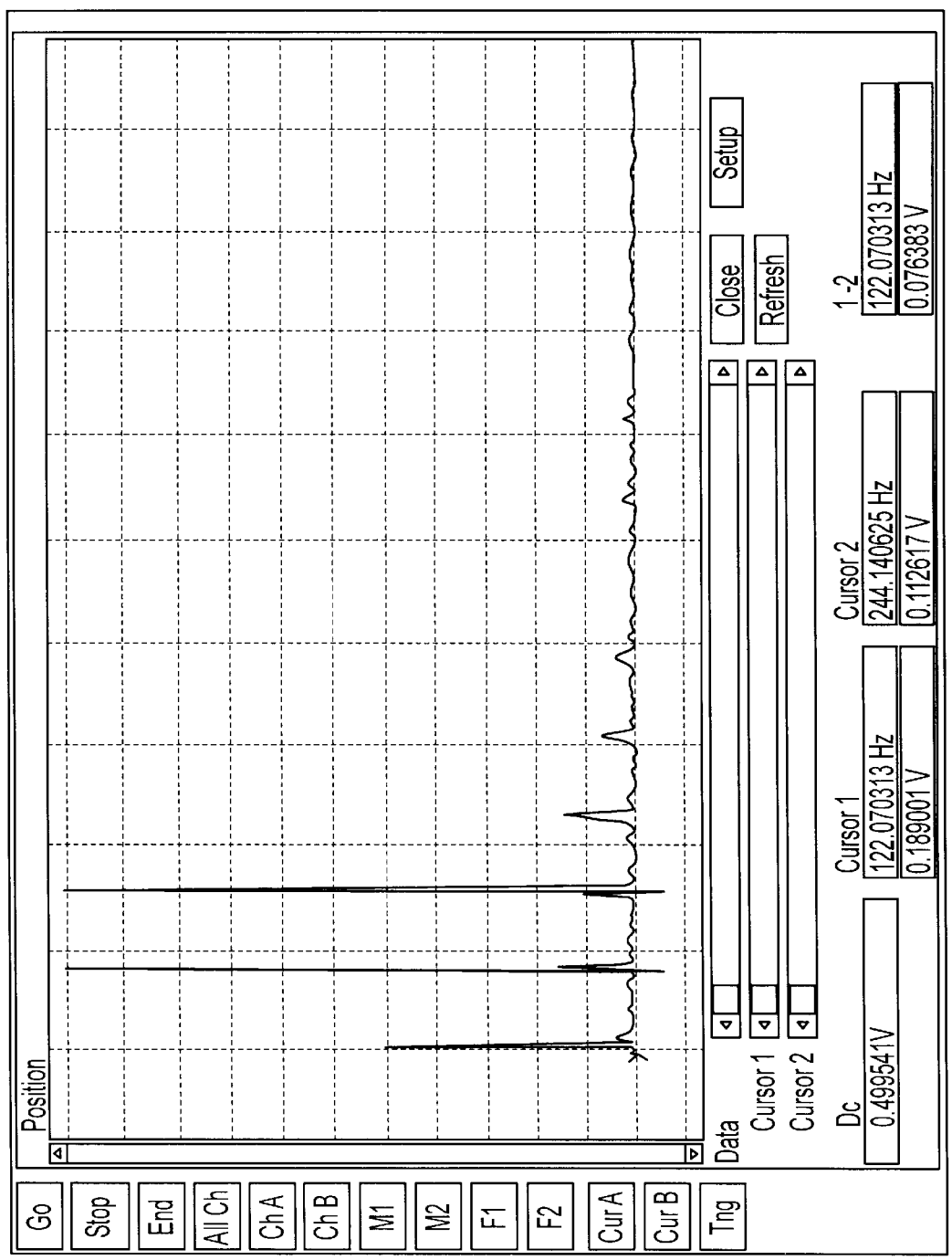
FIG. 14 illustrates a waveform of the magnitude of the peak current of the difference signals developed within the human body.
Figure 15:
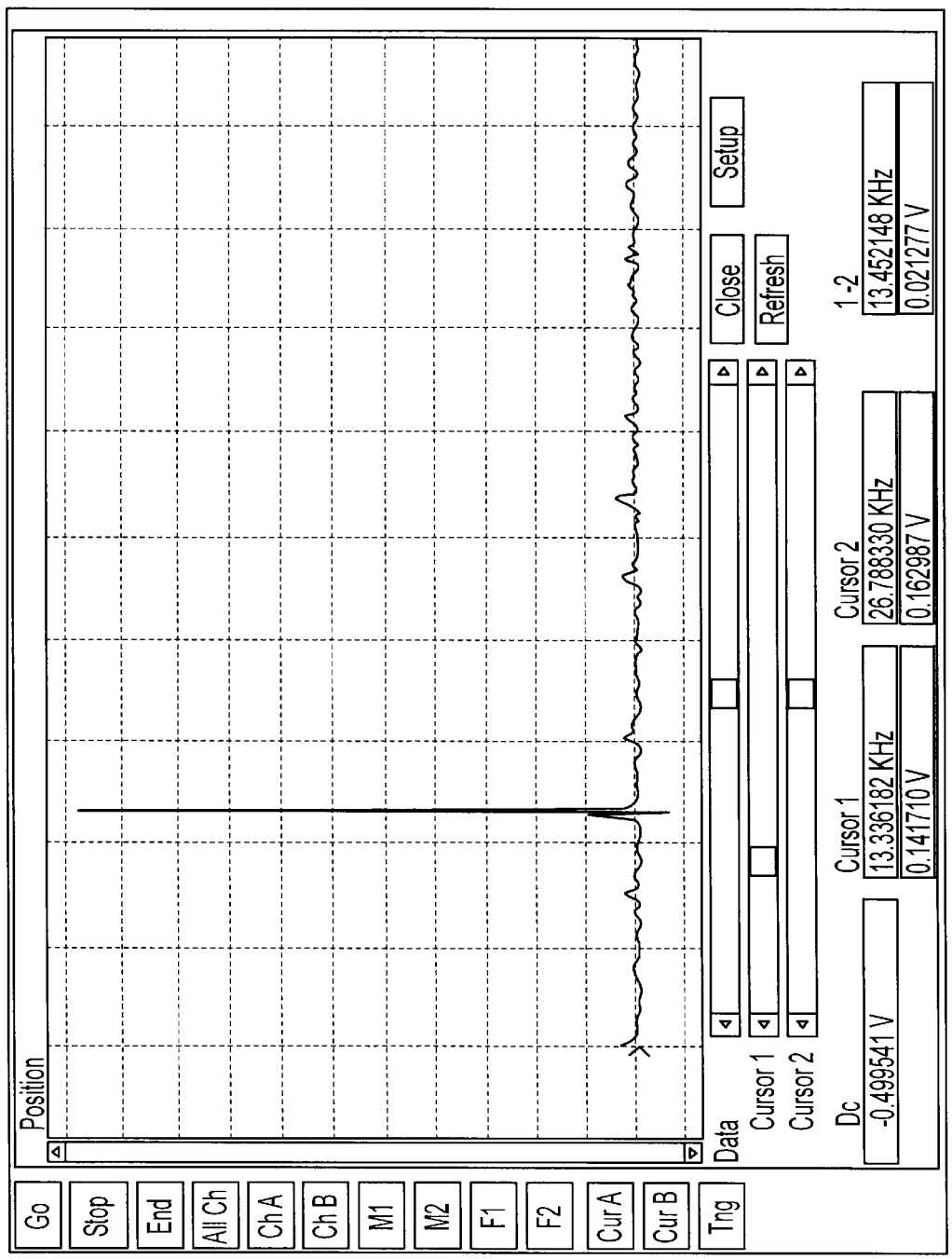
FIG. 15 illustrates a waveform of the sum signal derived in the same setup as FIG. 14.

FIG. 14 illustrates a waveform of the magnitude of the peak current of the difference signals developed within the human body. The current measured is from one electrode placed at the lowest abdominal quadrant and the other is placed 10 cm left of L5 on the back in an adult male subject. The second harmonic at 244 Hz is depressed by −45 db relative to the primary therapeutic signal at 122 Hz. FIG. 15 illustrates a waveform of the sum signal derived in the same setup as FIG. 14. As can be seen the signal frequency is well separated from the physiologically important frequency range.

Benefits of the Pain Control Apparatus

Benefits of the Pain Control Apparatus include:
a. Significant non-invasive pain control;
b. Dramatic increase in range of motion;
c. Reduction in the dosages of or elimination of the need for morphine and other narcotics;
d. Residual pain control and increased range of motion for up to 24 hours;
e. No known deleterious side effects;
f. Control by the patient of their own comfort level;
g. Reduction of risk by eliminating potential chemical allergic reactions and drug interaction problems;
h. Tactile sensory apparatus and awareness remains intact; and
i. Improvement in patient's quality of life.

Applications

There are a number of pain applications for the system including, but not limited to, acute and traumatic pain, chronic and arthritic pain, surgical pain, post-surgical pain, and cancer pain. Specific locations on the body which can be treated include: face, jaw, neck, back, shoulders, hips, arms, elbows, wrists, hands, fingers, legs, knees, ankles, feet, toes.

Other Applications

Other applications include:

Electronic Epidural for Childbirth. For childbirth, the electronic epidural system has in addition to the benefits of the pain control apparatuses, other important attributes as well:
a. Significant reduction of risk to the fetus and mother;
b. Apparatus can be doctor or patient controlled;
c. Mother retains tactile awareness and can assist normally with the delivery while the epidural is in place;
d. Electronic epidural can remain in place for the entire birthing process until the baby is delivered; and
e. Electronic epidural allows pain control for birth in parts of the world where conventional epidurals are not readily available.

Electronic Anesthesia for Dermatological Procedures. The system can be used to provide local anesthesia for skin surgery, wart removal, electrolysis, shaving, application of tattoos and other dermatological procedures.

Acceleration of Bone Growth. It has been known for quite some time that the application of an electric field through implanted electrodes can stimulate the rate of bone growth and rates of healing of bone. The electro-therapeutic apparatus can be used to deliver a precise electrical field non-invasively of the proper frequency content to a targeted region. This action would take place with better control of the electrochemically driven reactions around the targeted region. The system can be used to accelerate osseointegration non-invasively, i.e. reduce the time required for bone to grow into and bond with prosthetic apparatuses including dental implants, knees, and hips while simultaneously reducing postoperative pain. The apparatus also has the potential to accelerate the healing of broken bones non-invasively.

Cartilage Regrowth. Clinical Studies have been performed at University of Nebraska Medical Center and at Johns Hopkins University School of Medicine which have shown that TENS devices can cause cartilage growth in the knee. Since, unlike TENS, the disclosed system is able to deliver low frequency signals into deep tissue, it should in theory be able to cause cartilage growth much more effectively than TENS devices and as a result be much more efficacious. Advanced Hearing Aid Systems. The disclosed technology can be used in the audio frequency range and be tailored to deliver audio information to the cochlea in a safe and effective manner. Current cochlea-implanted hearing aid systems use pulsed DC signals to deliver the representation of audio information. Pulsed DC signals leads to nerve and cell damage over time. The disclosed technology allows information to be delivered into a volume of tissue including the cochlea with a DC-suppressed AC signal that significantly lessens the potential for nerve damage.

In this embodiment of the apparatus, the use of a PLL system allows the apparatus to have one channel modulated while another is fixed (FM modulation). The frequency modulation of the nth reference frequency allows the signal or envelope to convey information into the body of the patient. Additionally, the use of a slowly varying difference signal may lessen any effect of habituation if it is found during chronic use. Information exchange could be another big factor in the utility of the apparatus. Currently, cochlea implants for deafness rely on pulse stimulation to convey auditory information to the brain. These pulses, even with the use of DC blocking, still have a considerable DC component. This component can cause irreversible tissue damage via the production of chemical intermediates arising from the electrochemical effect of the DC current. However, the disclosed apparatus is a suppressed-DC AC signal generator whose resultant field should not have little or no net electrochemical effects. One way to affect the auditory informational transfer is to hold one frequency fixed and use the ambient audio level to vary the input level to the phase locked loop voltage control oscillator. The resulting signal would contain the auditory information. Theoretically, the nerves within the cochlea could operate on the signals and extract from the modulated beat the information that is a representation of an electrically converted acoustical field.

Accelerated and Targeted Drug Delivery. A consequence of the disclosed technology is that it causes increased blood flow in the volume of tissue at and beneath the treatment site. This technology might be employed as an adjunct to a chemical drug delivery system to accelerate and target the delivery of certain drugs into deep tissue.

Embodiments

The present invention can be embodied in the form of computer-implemented processes and apparatuses for practicing those processes. The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for this invention, but that the invention will include all embodiments falling within the scope of the appended claims.

What is claimed is:

1. An electro-therapy apparatus for providing therapeutic electric current to a treatment site of a patient comprising:
   a signal generator forming first and second signals having a frequency difference of between 1 Hz and 250 Hz, each signal having a frequency at least about 1 KHz;
   at least one feed electrode connected to the signal generator and adapted to output a therapeutic signal to at least one feed site on or beneath a first epidermal or mucous membrane surface of the patient; and
   at least one return electrode adapted to be positioned on or beneath a second epidermal or mucous membrane surface of the patient, locally to said treatment site;
   wherein:
   the first and second signals are sinusoidal alternating current signals;
   the therapeutic signal is formed from said first and second signals prior to being output to said at least one feed site; and
   only a single feed electrode is adapted to output said therapeutic signal.

2. The electro-therapy apparatus according to claim 1, wherein the at least one feed electrode comprises a feed electrode pad and the at least one return electrode comprises a return electrode pad.

3. The electro-therapy apparatus according to claim 2, wherein the feed electrode pad and the return electrode pad comprise a conductive material.

4. The electro-therapy apparatus according to claim 2, wherein the first and second signals are separately amplified and then summed at the first electrode pad to form the therapeutic signal.

5. The electro-therapy apparatus according to claim 2, wherein an area of the feed electrode pad exceeds an area of the return electrode pad.

6. The electro-therapy apparatus according to claim 5, wherein a ratio of the area of the feed electrode pad to the area of the return electrode pad is at least 2:1.

7. The electro-therapy apparatus according to claim 6, wherein a ratio of the area of the feed electrode pad to the area of the return electrode pad is at least 8:1.

8. The electro-therapy apparatus according to claim 1, wherein the first and second signals are substantially free of DC components.

9. An electro-therapy apparatus for providing therapeutic electric current to a treatment site of a patient comprising:
   a signal generator forming first and second signals having a frequency difference of between 1 Hz and 250 Hz, each signal having a frequency at least about 1 KHz;
   balanced amplifiers configured to minimize a DC component of said first and second signals;
   at least one feed electrode connected to the signal generator and adapted to output a therapeutic signal to at least one feed site on or beneath a first epidermal or mucous membrane surface of the patient; and
   at least one return electrode adapted to be positioned on or beneath a second epidermal or mucous membrane surface of the patient, locally to said treatment site;
   wherein:
   the first and second signals are sinusoidal alternating current signals;
   the therapeutic signal is formed from said first and second signals prior to being output to said at least one feed site.

10. An electro-therapy apparatus for providing therapeutic electric current to a treatment site of a patient comprising:
    a signal generator forming first and second signals having a frequency difference of between 1 Hz and 250 Hz, each signal having a frequency at least about 1 KHz;
    a DC-blocking capacitor positioned in a signal path of each of said first and second signals;
    at least one feed electrode connected to the signal generator and adapted to output a therapeutic signal to at least one feed site on or beneath a first epidermal or mucous membrane surface of the patient; and
    at least one return electrode adapted to be positioned on or beneath a second epidermal or mucous membrane surface of the patient, locally to said treatment site;
    wherein:
    the first and second signals are sinusoidal alternating current signals;
    the therapeutic signal is formed from said first and second signals prior to being output to said at least one feed site.

11. The electro-therapy apparatus according to claim 1, wherein the first and second signals are summed before being amplified.

12. The electro-therapy apparatus according to claim 1, wherein the therapeutic signal is a linear combination of said first and second signals.

13. The electro-therapy apparatus according to claim 12, wherein the therapeutic signal is a sum of said first and second signals.

14. The electro-therapy apparatus according to claim 1, wherein said first and second signals have a frequency difference of between 80 and 130 Hz.

15. The electro-therapy apparatus according to claim 14, wherein said first and second signals have a frequency difference of about 122 Hz.

16. The electro-therapy apparatus according to claim 14, wherein said first and second signals are at a frequency of about 8 kHz.

17. An electro-therapy apparatus for providing therapeutic electric current to a treatment site of a patient comprising:
a signal generator forming first and second signals having a frequency difference of between 1 Hz and 250 Hz, each signal having a frequency at least about 1 KHz;
at least one feed electrode connected to the signal generator and adapted to output a therapeutic signal to at least one feed site on or beneath a first epidermal or mucous membrane surface of the patient; and
at least one return electrode adapted to be positioned on or beneath a second epidermal or mucous membrane surface of the patient, locally to said treatment site;
wherein:
the first and second signals are sinusoidal alternating current signals;
the therapeutic signal is formed from said first and second signals prior to being output to said at least one feed site; and
said first and second signals are at a frequency of about 8 kHz.

18. The electro-therapy apparatus according to claim 1, wherein the frequency of the first signal is fixed.

19. The electro-therapy apparatus according to claim 18, wherein the frequency of second signal is variable.

20. The electro-therapy apparatus according to claim 1, configured to be carried by the patient.

21. The electro-therapy apparatus according to claim 1, configured to be worn or strapped to the patient.

22. The electro-therapy apparatus according to claim 1, wherein the signal generator comprises a microprocessor-controlled frequency control system.

23. The electro-therapy apparatus according to claim 22, further comprising a memory configured to store at least one amplitude setting associated with the therapeutic signal.

24. An electro-therapy apparatus for providing therapeutic electric current to a treatment site of a patient comprising:
a signal generator forming first and second signals having a frequency difference of between 1 Hz and 250 Hz, each signal having a frequency at least about 1 KHz, said signal generator comprising a microprocessor-controlled frequency control system;
at least one feed electrode connected to the signal generator and adapted to output a therapeutic signal to at least one feed site on or beneath a first epidermal or mucous membrane surface of the patient;
at least one return electrode adapted to be positioned on or beneath a second epidermal or mucous membrane surface of the patient, locally to said treatment site; and
a feedback system configured to monitor at least one of a voltage or a current associated with the patient's use of the apparatus, and control the therapeutic signal in response thereto;
wherein:
the first and second signals are sinusoidal alternating current signals;
the therapeutic signal is formed from said first and second signals prior to being output to said at least one feed site.

25. The electro-therapy apparatus according to claim 24, wherein the therapeutic signal is controlled so as to maintain a monitored voltage at a constant voltage level.

26. The electro-therapy apparatus according to claim 24, wherein the feedback system comprises:
a feedback circuit that monitors said at least one of a voltage and a current; and
software configured to determine whether a change in the therapeutic signal is required, based at least in part on at least one of said voltage and current.

27. The electro-therapy apparatus according to claim 26, wherein the feedback circuit comprises:
a resistor that monitors a current through the patient;
an amplifier for differentially detecting a voltage developed by said current passing through the resistor;
a gain block for further amplifying the detected voltage;
a buffered attenuator for sampling the voltage across the two electrodes and setting the voltage's value to within a predetermined range of an analog-to-digital (ADC) circuit to which the voltage is to be input;
an analog multiplexer having as a first input thereto an output of the gain block and having as a second input thereto an output of buffered attenuator, the analog multiplexer configured to selectively output either the first input or the second input, based on a signal from a CPU;
an RMS to DC converter having input thereto an output of the analog multiplexer, and being configured to output a DC level approximately equal to the RMS value of the applied signal;
an analog-to-digital converter configured to convert an analog output of the RMS to DC converter into a digital signal; and
a digital attenuator configured to change said output level, as required by the feedback system.

28. An electro-therapy apparatus for providing therapeutic electric current to a treatment site of a patient comprising:
a signal generator forming first and second signals having a frequency difference of between 1 Hz and 250 Hz, each signal having a frequency at least about 1 KHz;
at least one feed electrode connected to the signal generator and adapted to output a therapeutic signal to at least one feed site on or beneath a first epidermal or mucous membrane surface of the patient;
at least one return electrode adapted to be positioned on or beneath a second epidermal or mucous membrane surface of the patient, locally to said treatment site;
wherein:
the first and second signals are sinusoidal alternating current signals;
the therapeutic signal is formed from said first and second signals prior to being output to said at least one feed site;
said at least one feed electrode comprises a plurality of feed electrodes adapted to be positioned on the patient's body; and
the apparatus further comprises a first electronic switch configured to selectively apply the therapeutic signal to exactly one of said plurality of feed electrodes at any given instant.

29. The electro-therapy apparatus according to claim 28, wherein the first electronic switch is configured to switch between said plurality of feed electrodes during zero crossings of the therapeutic signal.

30. The electro-therapy apparatus according to claim 28, wherein the first electronic switch is configured to switch between said plurality of feed electrodes at a rate of 10–50 Hz.

31. An electro-therapy apparatus for providing therapeutic electric current to a treatment site of a patient comprising:
a signal generator forming first and second signals having a frequency difference of between 1 Hz and 250 Hz, each signal having a frequency at least about 1 KHz;

at least one feed electrode connected to the signal generator and adapted to output a therapeutic signal to at least one feed site on or beneath a first epidermal or mucous membrane surface of the patient;

at least one return electrode adapted to be positioned on or beneath a second epidermal or mucous membrane surface of the patient, locally to said treatment site;

wherein:

the first and second signals are sinusoidal alternating current signals;

the therapeutic signal is formed from said first and second signals prior to being output to said at least one feed site;

said at least one return electrode comprises a plurality of return electrodes adapted to be positioned on the patient's body; and the apparatus further comprises a first electronic switch configured to selectively activate exactly one of said plurality of return electrodes at any given instant.

32. The electro-therapy apparatus according to claim 31, wherein the first electronic switch is configured to switch between said plurality of return electrodes during zero crossings of the therapeutic signal.

33. The electro-therapy apparatus according to claim 31, wherein the first electronic switch is configured to switch between said plurality of return electrodes at a rate of 10–50 Hz.

34. The electro-therapy apparatus according to claim 31, comprising:

a plurality of feed electrodes adapted to be positioned on the patient's body; and an second electronic switch configured to selectively apply the therapeutic signal to exactly one of said plurality of feed electrodes at any given instant.

35. The electro-therapy apparatus according to claim 34, wherein the second electronic switch is configured to switch between said plurality of feed electrodes during zero crossings of the therapeutic signal.

36. The electro-therapy apparatus according to claim 34, wherein the second electronic switch is configured to switch between said plurality of feed electrodes at a rate of 10–50 Hz.

* * * * *

UNITED STATES PATENT AND TRADEMARK OFFICE
CERTIFICATE OF CORRECTION

PATENT NO. : 6,584,358 B2
DATED : October 27, 2003
INVENTOR(S) : Carter et al.

It is certified that error appears in the above-identified patent and that said Letters Patent is hereby corrected as shown below:

Column 4,
Delete lines 22-23.

Column 11,
Delete lines 28-46.

Signed and Sealed this

Twenty-ninth Day of June, 2004

JON W. DUDAS
*Acting Director of the United States Patent and Trademark Office*